US005700642A

United States Patent [19]
Monforte et al.

[11] Patent Number: 5,700,642
[45] Date of Patent: Dec. 23, 1997

[54] OLIGONUCLEOTIDE SIZING USING IMMOBILIZED CLEAVABLE PRIMERS

[75] Inventors: Joseph Albert Monforte, Berkeley; Christopher Hank Becker, Menlo Park; Thomas Andrew Shaler, San Francisco; Daniel Joseph Pollart, Menlo Park, all of Calif.

[73] Assignee: SRI International, Menlo Park, Calif.

[21] Appl. No.: 445,751

[22] Filed: May 22, 1995

[51] Int. Cl.⁶ .............................. C12Q 1/68; C12P 19/34
[52] U.S. Cl. .................................... 435/6; 435/91.2
[58] Field of Search ................... 435/6, 91.2; 536/22.1, 536/24.33; 436/173; 937/77; 250/287

[56] References Cited

U.S. PATENT DOCUMENTS

| | | | |
|---|---|---|---|
| 4,775,619 | 10/1988 | Urdea | 435/6 |
| 4,818,681 | 4/1989 | Dattagupta | 435/6 |
| 5,106,585 | 4/1992 | Minami et al. | 422/68.1 |
| 5,118,605 | 6/1992 | Urdea | 435/6 |
| 5,288,644 | 2/1994 | Beavis et al. | 436/94 |
| 5,405,746 | 4/1995 | Uhlen | 435/6 |
| 5,547,835 | 8/1996 | Koster | 435/6 |

FOREIGN PATENT DOCUMENTS

| | | |
|---|---|---|
| 0227772 | 6/1986 | European Pat. Off. |
| 0 360 676 | 9/1989 | European Pat. Off. |
| WO 90/04649 | 10/1989 | WIPO |
| WO89/12694 | 12/1989 | WIPO |
| WO 91/11533 | 1/1991 | WIPO |
| WO92/05287 | 4/1992 | WIPO |
| WO 93/13220 | 12/1992 | WIPO |
| WO 94/16101 | 1/1994 | WIPO |

OTHER PUBLICATIONS

Bahr, U., et al., "Analysis of Biopolymers by Matrix-Assisted Laser Desorption/Ionization (MALDI) Mass Spectrometry," *Fresenius J. Anal. Chem.* 348:783–791 (1994).

Barinaga, M., "Protein Chemists Gain a New Analytical Tool," *Science* 246:32–33 (1989).

Brummel, C.L., et al., "A Mass Spectrometric Solution to the Address Problem of Combinatorial Libraries," *Science* 264:399 (1994).

Fitzgerald, M.C., et al., "The Analysis of Mock DNA Sequencing Reactions Using Matrix-Assisted Laser Desorption/Ionization Mass Spectrometry,"*Rapid Comm. in Mass Spectrom.* 7:895–897 (1993).

Goldkorn, T., and Prockop, D.J., "A Simple and Efficient Enzymatic Method for Covalent Attachment of DNA to Cellulose: Application for Hybridization-Restriction Analysis and for In Vivo Synthesis of DNA Probes," *Nuc. Acids. Res.* 14:9171 (1986).

Hettich, R.L., and Buchanan, M.V., "Determination of Oligonucleotide Sequences and Modifications by Laser Desorption Fourier Transform Mass Spectrometry," *Abst. Pap. Am. Chem. Soc.* 200:1-2, Abstract 105 (1990).

Hillenkamp, F., and Karas, M., "Matrix Assisted UV-Laser Desorption/Ionization: A New Approach to Mass Spectrometry of Large Biomolecules" in *Biological Mass Spectrometry* (Burlingame, A.L., and McCloskey, J.A., Eds.), Elsevier Science Publishers B.V., Amerstam, Holland (1988).

Hillenkamp, F., and Karas, M., "Laser Desorption Ionization of Proteins with Molecular Masses Exceeding 10,000 Daltons," *Anal. Chem.* 60:2299–2301 (1988).

Hillenkamp, F., and Karas, M., "Matrix Laser Desorption of Very Large Organic Molecules" in *Mass Spectrometry of Large Non-Volatile Molecules for Marine Organic Chemistry* (Hilf, E.R., and Tuszynski, W., Eds.) World Scientific Publishers, Singapore, (1990).

Lay, Jr., J.O., et al., "Detection and Characterization of DNA Adducts at the Femtomole Level by Desorption Ionization Mass Spectrometry," *Environ. Health Perspect.* 99:191–193 (1993).

Mag, M., et al., "Synthesis and Selective Cleavage of an Oligodeoxynucleotide Containing a Bridged Internucleotide 5'-Phosphorothioate Linkage," *Nuc. Acids Res.* 19(7):1437–1441 (1991).

Maskos, U., and Southern, E.M., "Oligonucleotide Hybridisations on Glass Supports: A Novel Linker for Oligonucleotide Synthesis and Hybridisation Properties of Oligonucleotides Synthesis In Situ," *Nuc. Acids Res.* 20(7):1679–1684 (1992).

Nadji, S., et al., "Photochemically and Photoenzymatically Cleavable DNA," *J. Am. Chem.* 114:9266–9269 (1992).

Nordhoff, E., et al., "Matrix-Assisted Laser Desorption/ Ionization Mass Spectrometry of Nucleic Acids with Wavelengths in the Ultraviolet and Infrared," *Rapid Comm. in Mass Spectrom.* 6:771–776 (1992).

Parr, G.R., et al., "Matrix-Assisted Laser Desorption/Ionization Mass Spectrometry of Synthetic Oligodeoxyribonucleotides," *Rapid Comm. in Mass Spectrom.* 6:369–372 (1992).

Stemmler, E.A., et al., "Matrix-Assisted Laser Desorption/ Ionization Fourier-Transform Mass Spectrometry of Oligodeoxyribonucleotides," *Rapid Comm. in Mass Spectrom.* 7:828–836 (1993).

Tang, K., et al., "Mass Spectrometry of Laser-Desorbed Oligonucleotides," *Rapid Comm. in Mass Spectrom.* 6:365–368 (1992).

(List continued on next page.)

*Primary Examiner*—Eggerton A. Campbell
*Attorney, Agent, or Firm*—Susan T. Evans; Gary R. Fabian

[57] ABSTRACT

The present invention provides modified oligonucleotide primers that (i) are designed for attachment to a solid support in a manner that does not block the ability to extend the primer from its 3' end, and (ii) incorporate a cleavable moiety so that a 3' portion of the primer (linked to an extension product) can be released from an immobilized 5' portion. Upon selective cleavage of the cleavable site, a large portion of the primer fragment remains affixed to the solid support. This enables the release of primer extension products that contain about five or fewer base pairs of the primer sequence, to provide more useful sizing and sequence information per fragment than extension products containing the entire primer.

19 Claims, 14 Drawing Sheets

OTHER PUBLICATIONS

Tang, K., et al., "Laser Mass Spectrometry of Oligonucleotides with Isomer Matrices," *Rapid Comm. in Mass Spectrom.* 7:435–439 (1993).

Tong, X., and Smith, L.M., "Solid Phase Purification in Automated DNA Sequencing," *J. DNA Seq. and Mapping* 4:151–162 (1993).

Wu, K.J., et al., "Matrix–Assisted Laser Desorption Time–of–Flight Mass Spectrometry of Oligonucleotides Using 3–Hydroxypicolinic Acid as an Ultraviolet–Sensitive Matrix," *Rapid Comm. in Mass Spectrom.* 7:142–146 (1993).

Wu, K.J., et al., "Time–of–Fight Mass Spectrometry of Underivatized Single–Stranded DNA Oligomers by Matrix–Assisted Laser Desorption," *Anal. Chem.* 66:1637–1645 (1994).

Youngquist, R.S., et al., "Matrix–Assisted Laser Desorption Ionization for Rapid Determination of the Sequences of Biologically Active Peptides Isolated from Support–Bound Combinatorial Peptide Libraries," *Rapid Comm. in Mass Spectrom.* 8:77–81 (1994).

Silveira, M.H., and L.E. Orgel, "PCR with detachable primers," *Nucleic Acids Research* 23(6): 1083–1084 (1995).

Frohman, M.A., "Cloning PCR Products," Chapter 2 in *The Polymerase Chain Reaction* (Mullis, K.B., et al., eds., Birkhauser Boston, 1994, pp. 14–37).

Szybalski, W., "Universal restriction endonucleases: designing novel cleavage specificities by combining adapter oligodeoxynucleotide and enzyme moieties," *Gene* 40: 169–173 (1985).

Nakamaye, K., et al., Direct Sequencing of polymerase chain reaction amplified DNA fragments through the incorporation of deoxynucleoside a–thiotriphosphates, Nuc. Acids Res. 16(21):9947–9959, 1988.

Biotin ∼∼∼ Streptavidin     Fig. 2L

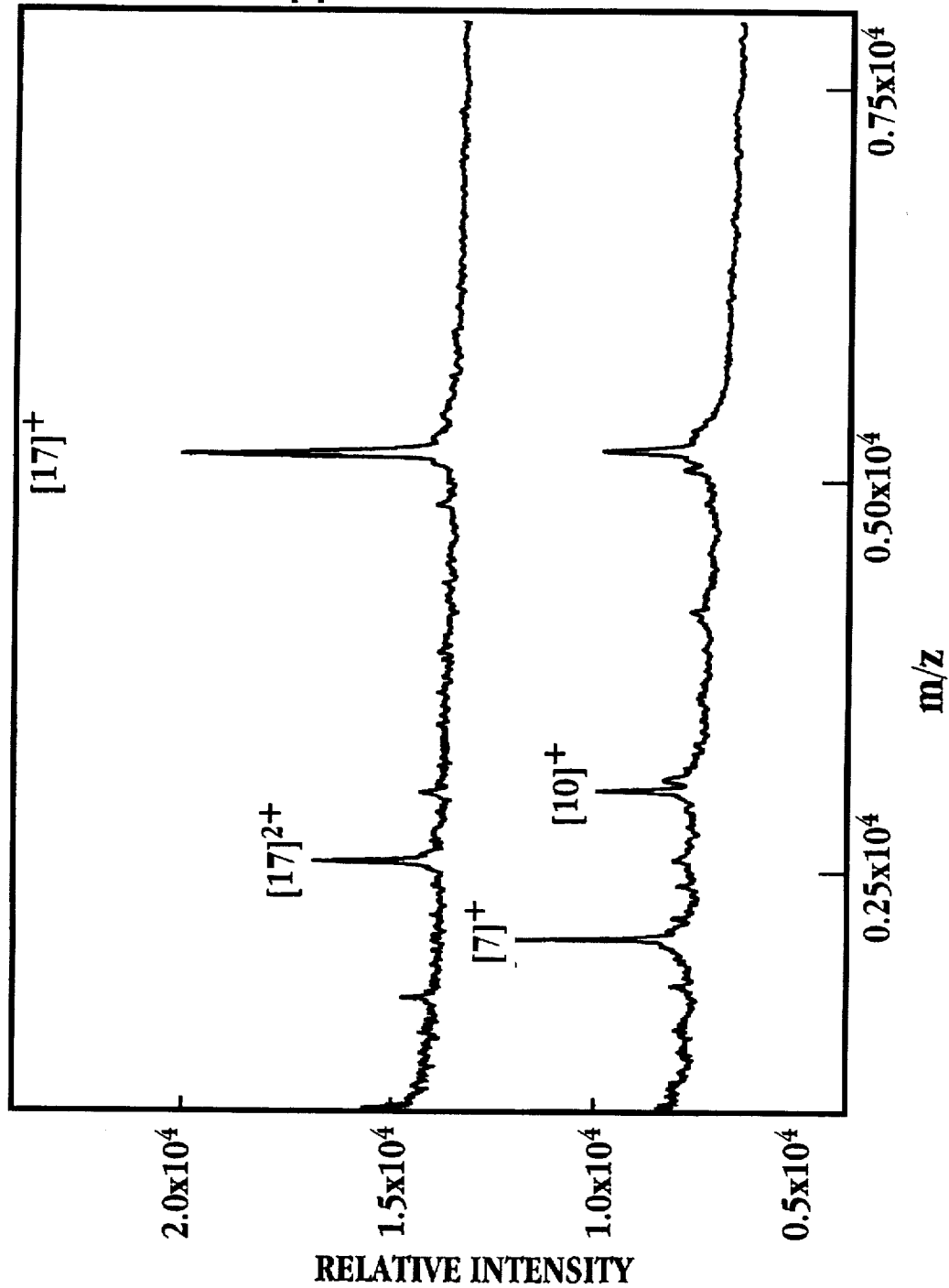

| TYPE OF HEMOGLOBIN | AMINO ACID SEQUENCE AND DNA NUCLEOTIDE SEQUENCE |
|---|---|
| A | -Pro-Glu-Glu<br>-CCT-G<u>A</u>G-GAG- |
| B | -Pro-Val-Glu<br>-CCT-G<u>T</u>G-GAG- |

Fig. 7A

| CONDITION | AMINO ACID SEQUENCE AND DNA NUCLEOTIDE SEQUENCE |
|---|---|
| NORMAL | 342<br>-Thr-Ile-Asp-Glu-Lys-Gly-Thr-<br>-ACC-ATC-GAC-<u>G</u>AG-AAA-GGG-A... |
| α₁-ANTITRYPSIN DEFICIENT | -Thr-Ile-Asp-Lys-Lys-Gly-Thr-<br>-ACC-ATC-GAC-<u>A</u>AG-AAA-GGG-A... |

Fig. 7B

ABLE PRIMERS

FIELD OF THE INVENTION

The present invention relates to oligonucleotide compositions containing immobilized cleavable primers and diagnostic and analytical methods employing such primers.

REFERENCES

Agrawal, S., and Goodchild, J., *Tetrahedron Lett.* 28:3539–3542 (1987).
Ausubel, F.M ., et al., *Current Protocols In Molecular Biology*, John Wiley and Sons, Inc., Media PA.
Bannwarth, W., et al., *DNA* 5:413 (1986).
Bannwarth, W., *Chimia* 41:302 (1987).
Bannwarth, W., *Helvetica Chimica Acta* 71:1517–1527 (1988).
Bischoff, R., et al., *Analytical Biochemistry* 164:336–344 (1987).
Collins, S. J., et al., *Science* 225:72 (1984).
Cormier, J., et al., *Nucleic Acids Res.* 16:4583–4594 (1988).
Corey, E. J., and Snider, B. B., *J. Am. Chem. Soc.* 94:2549–2550 (1972).
Cosstick, R. et al., *J. Chem. Soc., Chem. Comm* 992 (1988).
Cosstick, R., et al., *Tetrahedron Letters* 30 (35):4693–4696 (1989).
Daley, G. Q., et al., *Proc. Natl. Acad. Sci. USA* 85:9312–9316 (1988).
Dattagupta, N., U.S. Pat. No. 4,818,681 (1989).
Erlich, H. A., PCR TECHNOLOGY, Stockton, New York (1989).
Fodor, S. P. A., et al., *Science* 251:767–773 (1991).
Gale, R. P., et al., *Proc. Natl. Acad. Sci. USA* 81:5648 (1984).
Ghosh, S., et al., *Nucleic Acids Research* 15:5353–5372 (1987).
Gingeras, T., et al., *Nucleic Acids Research* 15:5373–5390 (1987).
Glazer, A., et al., *Nature* 359:859–861 (1992).
Goldkorn, T., et al., *Nucleic Acids Research*, 14(22):9171–9191 (1986).
Green, N. M., In: ADVANCES IN PROTEIN CHEMISTRY (Avidin, Ed.) Academic Press, New York, N.Y., U.S.A., p. 29, 85–133 (1975).
Gromova, E. S., *Bioorg. Khim* 13:269 (1987).
Gyllensten, U. B., *BioTechniques* 7:700 (1989).
Hasa, T., et al., *Chem Lett* 601 (1976).
Hegner, M., et al., *FEBS Letters* 336:452–456 (1993a).
Hegner, M., et al., *Surface Sci.* 291:39–46 (1993b)
Hillenkamp, R., *Adv. Mass Spectrometry* 11A:354–361 (1988).
Hobbs, J. B., *Oranophosphorous Chem.* 21:201–321 (1990).
Innis, M. A., et al., PCR PROTOCOLS, Academic Press, San Diego (1990).
Khrapko, K., et al., *DNA Sequence*, 1:375–388 (1991).
Koole, L. H., et al., *Proc. K. Ned. Akad. Wet.* B91:205–209 (1988).
Kremsky, J., et al., *Nucleic Acids Research* 15:2891–2909 (1987).
Kusukawa, N., et al., *BioTechniques*, 9:66 (1990).
Mag, M., et al., *Nucleic Acids Research* 19 (7): 1437–1441 (1991).
Maniatis, T., et al., MOLECULAR CLONING: A LABORATORY MANUAL, Cold Spring Harbor Laboratory (1982).
Maskos, U., et al., *Nucleic Acids Research* 20(7):1679–1684 (1992).
McBride, L. J., et al., *Tetrahedron Lett.* 24:245 (1983).
Miller, P. S., et al., *J. Am. Chem. Soc.* 93:6657–6665 (1971).
Moody, H. M., et al., *Nucleic Acids Research* 12:4769–4782 (1989).
Mullis, K. B., et al., U.S. Pat. No. 4,683,195, issued 28 Jul. 1987.
Mullis, K. B., U.S. Pat. No. 4,683,202, issued 28 Jul. 1987.
Nadji, S., et al., *J. Am. Chem. Soc.* 114:9299–9269 (1992).
Nakamaye, K. I., et al., *Nucleic Acids Research* 16:9947–9959 (1988).
Nelson, R. W., et al., *Science*, 246:1585–1587 (1989).
Ogilvie, K., et al., *Tetrahedron Lett.* 26:4159–4162 (1986).
Olsen, D., et al., *Methods in Enzymology*. 218:79–92 (1993).
Olsen, G. J., et al., *Nucleic Acids Res.* 20:2199 (1992).
Primings, et al., *Methods in Enzymology* 65:561–580 (1980).
Saha, A., et al., *J. Org. Chem*, 58:7827–7831 (1993).
Sanger, F., *J. of Molecular Biology* 94:441–448 (1975).
Saiki, R. K., et al., *Proc. Natl Acad. Sci.*, 86:6230–6234 (1989).
Schmidt, T. M., et al., *Methods in Enzymology* 235:205–222 (1994).
Seliger, H., et al., *Nucleosides Nucleotides* 6:483–484 (1987).
Southern, et al., *Genomics* 13:1008–1017 (1992).
Sproat, B. S., et al., *Nucleic Acids Res.* 15:4837 (1987).
Szczylik, C., et al., *Science* 253:562–565 (1991).
Tomasz, J., et al., *Tetrahedron Lett.* 22:3905–3908 (1981).
Townsend, L. B., et al., Eds., in Nucleic ACID CHEMISTRY: IMPROVED AND NEW SYNTHETIC PROCEDURES, METHODS, AND TECHNIQUES, John Wiley and Sons, New York, N.Y., pp. 337 (1986).
Van Ness, J. et al., *Nucleic Acids Res.* 19:3345–3350 (1991).
Wu, K. J., et al., *Rapid Communications in Mass Spectrometry* 7:142–146 (1993).
Watson, J. D., et al., RECOMBINANT DNA Second Ed., Scientific American, Inc., Chapter 27 (1992).
Yamamoto, I., et al., *J. Chem. Soc., Perkin Trans.* 1, 1:306 (1980).
Youngquist, R. S., et al., *Rapid Communications in Mass Spectrometry* 8:77–81 (1994).
Zhang, Y., et al., *Nucleic Acids Res.*, 19:3929–3933 (1991).

BACKGROUND OF THE INVENTION

DNA, the primary genetic material, is a complex molecule consisting of two intertwined polynucleotide chains, each nucleotide containing a deoxyribose unit, a phosphate group and a nitrogenous heterocyclic base. The two polynucleotide strands are held together via hydrogen bonding interactions between complementary base pairs.

A normal human being possesses 23 pairs of chromosomes containing a total of about 100,000 genes. The length of DNA contained within the human chromosomes totals about 3.3 billion base pairs, with a typical gene containing about 30,000 base pairs.

Due to the vast amount of genetic information yet to be gathered in both human and non-human genomes, intense efforts are underway to develop new and faster methods of DNA detection, sizing, quantification, sequencing, and gene identification including the mapping of human disease genes. Although the efficiency of these processes has been improved by automation, faster and cheaper methods must still be developed to efficiently carry out genomic-scale DNA analyses.

Oligonucleotide sizing and sequence analysis is typically carried out by first utilizing either the enzymatic method developed by Sanger and Coulson, or by chemical degradation, developed by Maxam and Gilbert. The Sanger method uses enzymatic chain extension coupled with chain terminating dideoxy precursors to produce randomly terminated DNA fragments. The Maxam and Gilbert technique involves four different basespecific reactions carried out on portions of the DNA target to produce four sets of radiolabeled fragments. Both techniques utilize gel electrophoresis to separate resultant DNA fragments of differing lengths.

In conventional DNA analysis, the DNA fragments are labeled with radioisotopes. After separation on sequencing gels, the fragments are visualized by the image they generate upon a piece of film applied to the gel.

Other methods of DNA analysis have been described which eliminate the use of radioisotopes. One example of such a method uses fluorophores or fluorescent tags. In general, four different fluorophores, each having a different absorption and emission spectrum, are attached to the DNA primers using chemical DNA synthesis techniques. Primers with different fluorescent labels are used in each of the four enzymatic sequencing reactions.

In an alternate approach to four dye fluorescence-based detection, a dye is chemically attached to a chain-terminating base analog after enzymatic extension. In this approach, synthesis of the different dye-primers is avoided.

Mono and polyfunctional intercalator compounds have also been developed as reagents for high-sensitivity fluorescence detection (Glazer, et al., 1992). These planar aromatic fluorophores (e.g., ethidium homodimer, thiazole orange homodimer, oxazole yellow homodimer) insert between adjacent base pairs of double stranded DNA.

Efforts to analyze DNA have been greatly aided by the development of a process for in vitro amplification of DNA, namely, the polymerase chain reaction (PCR). PCR provides the ability to amplify and obtain direct sequence information from as little as one copy of a target DNA sequence.

Typically, PCR amplification is carried out by placing a mixture of target double stranded DNA, a mixture of deoxynucleoside triphosphates, buffer, two primers (one phosphate-labeled) and DNA polymerase (e.g., heat stable Taq polymerase) in a thermocycler which cycles between temperatures for denaturation, annealing, and synthesis. The selection of primers defines the region to be amplified. In the first stage of the cycle, the temperature is raised to separate the double-stranded DNA strands to form the single-stranded templates for amplification. The temperature is then lowered to generate the primed templates for DNA polymerase. In a third stage, the temperature is raised to promote Taq-promoted DNA synthesis, and the cycle of strand separation, annealing of primers, and synthesis is repeated for about as many as 30–60 cycles.

Standard detection, sizing, and sequencing methods as described above, while providing useful information, are often tedious and costly. Many of the commonly employed techniques involve multiple handling steps. Further, the most common method of fragment analysis, gel electrophoresis, is a relatively time-consuming process.

SUMMARY OF THE INVENTION

The present invention provides an oligonucleotide composition containing a modified primer having a 5' end and a 3' end and containing at least one selectively clearable site. The modified primer further contains an immobilization attachment site typically located at the 5' end or 5' relative to the cleavable site. Preferably, the cleavable site is located at or within about five nucleotides from the 3' end of the primer.

The primer is attachable to a solid support by a linkage between the solid support and the primer immobilization attachment site to provide an immobilized modified oligonucleotide composition. In one embodiment, the primer is attached to the solid support via an intervening spacer arm, with a typical spacer being six or more atoms in length.

The modified oligonucleotide primer, which has a 5' end and a 3' end, is composed of two separate nucleotide regions. The first region contains the 5' end of the primer and an immobilization attachment site for binding to a solid support. The second region contains the 3' end of the primer, where the 3' end is capable of serving as a priming site for enzymatic extension, typically by a polymerase or ligase. The second region also contains a cleavable site which connects the first and second primer regions. In a preferred embodiment, the first region of the primer contains at least three nucleotides.

In one embodiment of the invention, the cleavable site is located at or within about five nucleotides from the 3' end of the primer. In an alternate embodiment, the second primer region consists of a single nucleotide that also contains the cleavable site, such as a ribonucleotide. The second region may alternatively be composed of only the clearable site.

Cleavable sites contained within the modified primer composition include dialkoxysilane, 3'-(S)-phosphorothioate, 5'-(S)-phosphorothioate, 3'-(N)-phosphoramidate, 5'-(N)-phosphoramidate, and ribose. Solid supports for use in the present invention include glass, silicon, polystyrene, aluminum, steel, iron, copper, nickel, and gold.

In one embodiment, the modified primers of the present invention are oligonucleotides, such as DNA or RNA, having phosphodiester internucleotide linkages. In another embodiment, the modified primers are oligonucleotide analogues composed of alternative backbone structures containing internucleotide linkages such as methylphosphonate, phosphotriester, phosphorothioate, and the like. Primers for use in the invention should be capable of hydrogen bonding in a sequence-specific manner to a target sequence.

The invention also provides a method for determining the size of a primer extension product. In employing the method, oligonucleotide size analysis is carried out by first contacting a modified primer of the present invention with a target nucleic acid molecule (e.g., DNA or RNA) to effect hybridization of the primer with the single stranded target. The modified primer is complementary to the target and has a first region containing an immobilization attachment site and a second region containing the 3' end of the primer, where the 3' end is capable of serving as a priming site for enzymatic extension. The second region of the primer also contains a cleavable site.

Returning to the method for determining the size of a primer extension product, the primer is then extended by enzymatic means, typically by action of a polymerase or ligase, to generate a mixture containing a product composed of the primer and an extension segment. The resulting product, in immobilized form, is cleaved at the cleavable site and the resulting extension segment is then sized by any of a number of suitable analytical techniques, preferably mass spectrometry. Optionally, the immobilized product is washed prior to cleavage at the cleavable site, allowing ready removal of all non-immobilized species from the reaction mixture prior to sizing of the extension segments.

The primer may be attached to the immobilization attachment site either prior to or after enzymatic extension. The immobilization attachment remains intact under the selected cleavage conditions to retain a significant portion of nucleotides from the modified primer (e.g., those comprising the first primer region) in immobilized form. In accordance with the present method, the read length of the extension segment resulting from cleavage at the cleavable site is increased relative to the read length of the product composed of the primer and the extension segment.

In one embodiment of the invention, the extension segments, typically containing no more than about five nucleotides derived from the modified oligonucleotide primer, are sized using mass spectrometry. Such sizing may utilize time-of-flight mass spectrometry, and more particularly, may be accomplished using matrix-assisted laser desorption ionization mass spectrometry.

The sizing method may also be coupled with amplification of a target nucleic acid.

In this aspect of the invention, first and second primers are combined with a target nucleic acid under conditions effective to promote the hybridization of the primers to the nucleic acid to generate primer/nucleic acid complexes. One of the primers (e.g., the first primer) is complementary to the target nucleic acid and has a first region containing the 5' end of the primer and an immobilization attachment site. The first primer further contains a second region containing the 3' end of the primer, where the 3' end is capable of serving as a priming site for enzymatic extension. The second region of the first primer further contains a cleavable site. The second primer is homologous to the target nucleic acid.

The primer/nucleic acid complexes are converted to double-strand fragments in the presence of a suitable polymerase and all four deoxynucleotide triphosphates (dNTPs). The number of primer-containing fragments is amplified by successively repeating the steps of (i) denaturing the double-strand fragments to produce single-strand fragments, (ii) hybridizing the single strands with the primers to form strand/primer complexes, (iii) generating double-strand fragments from the strand/primer complexes in the presence of a polymerase and all four dNTPs, and (iv) repeating steps (i) to (iii) until a desired degree of amplification has been achieved.

The amplified fragments are then denatured to generate a mixture including a product composed of the first primer and an extension segment. In one embodiment of this aspect of the invention, the amplified fragments containing the first primer are immobilized at the immobilization attachment site and the non-immobilized amplified fragments are removed, typically by washing. The first primer is then cleaved from the immobilized product at the cleavable site, causing the release of the extension segment from the support.

In an alternate embodiment, the amplified fragments may be immobilized prior to denaturing. Generally, the amplified fragments are immobilized prior to cleaving at the cleavable site, to enable release and subsequent analysis of the extension segments resulting from such cleavage, in the absence of other species (e.g., primers, reactants, excess dNTPs).

The extension segments are then sized by mass spectrometry. The read length of the extension segment is increased relative to the read length of the product composed of the first primer and the extension segment.

In a related aspect, a method is provided that utilizes the modified primers of the invention for determining the sequence of a target molecule by mass spectrometry. In one embodiment of this aspect of the invention, the sequence of a target nucleic acid is determined by hybridizing a modified immobilizable primer of the present invention with a target nucleic acid, such as DNA or RNA, followed by enzymatically extending the primer in the presence of a first of four different dideoxy nucleotides to generate a mixture of primer extension products. The primer extension products each contain a primer and an extension segment. The extension products are denatured, immobilized, and washed to remove non-immobilized species present in the reaction. As in the embodiments described above, immobilization can occur before or after enzymatic extension, and is typically carried out prior to cleavage at the cleavable site. Subsequent to immobilization and removal of non-immobilized species, the primer extension products are cleaved to release the extension segments. The extension segments are sized by mass spectrometry, and the above steps are repeated with each of the remaining different dideoxy nucleotides. The sequence of the target is then determined by comparing the sizes of the extension segments obtained from each of the four extension reactions. Sequencing can also be carried out using the modified primers of the invention coupled with alternate sequencing methodologies which do not employ dideoxynucleotides.

In one such embodiment, the sequence of a target nucleic acid, such as DNA or RNA, is determined by first hybridizing a primer with a target DNA, where the primer (i) is complementary to the target DNA; (ii) has a first region containing the 5' end of the primer and an immobilization attachment site, and (iii) has a second region containing the 3' end of the primer and a cleavable site. The 3' end of the primer is also capable of serving as a priming site for enzymatic extension.

The primer is then extended with an enzyme in the presence of a first of four different deoxynucleoside α-thiotriphosphate analogs (dNTPαS) to generate a mixture of primer extension products containing phosphorothioate linkages. The phosphorothioate-containing extension products are then treated with a reagent that cleaves specifically at the phosphorothioate positions. Suitable reagents for promoting phosphorothioate-specific cleavage include exonuclease, 2-iodoethanol, and 2,3-epoxy-1-propanol. Treating of the extension products is typically carried out under conditions that produce limited cleavage of the phosphorothioate linkages, resulting in the production of a group of primer extension degradation products.

The primer extension degradation products are immobilized at the immobilization attachment sites to produce immobilized primer extension degradation products, each containing a primer and an extension segment. In alternative embodiments of this aspect of the invention, immobilization may be carried out either i) prior to enzymatic extension, ii) after enzymatic extension, or iii) prior to treating the phosphorothioate-containing primer extension products with a phosphorothioate-specific cleaving reagent.

Subsequent to immobilization, the primer extension degradation products are washed to remove non-immobilized species. Cleavage at the cleavable site results in the release of extension segments, which are then sized by mass spectrometry. Using the sequencing method of this aspect of the invention, the read length of any given extension segment is increased relative to the read length of its corresponding primer extension degradation product.

The steps of hybridization, enzymatic extension, treatment with a phosphorothioate-cleaving reagent, immobilization, washing, cleaving, and sizing are then repeated with a second, third, and fourth of the four different dNTPαS analogs to determine the sequence of the target DNA by comparison of the sizes of the extension segments obtained from each of the four extension reactions.

These and other objects and features of the invention will become more fully apparent when the following detailed description is read in conjunction with the accompanying figures and examples.

BRIEF DESCRIPTION OF THE FIGURES

FIGS. 2A–2M include a number of exemplary immobilization attachment linkages for use in immobilizing the 5' end of a modified oligonucleotide primer;

FIGS. 3A and 3B illustrate time-of-flight mass spectra for samples of a modified oligonucleotide primer containing a cleavable ribose desorbed from a solid matrix of 3-hydroxypicolinic acid both before and after selective cleavage;

FIGS. 7A and 7B illustrate the respective single gene mutation sites identified for two distinct genetic disorders suitable for detection using the modified primers of the present invention.

DETAILED DESCRIPTION OF THE INVENTION

I. DEFINITIONS

Figure 1A:
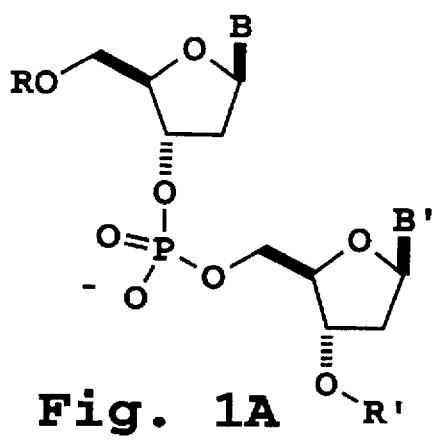
FIGS. 1A–1W show a native phosphodiester internucleotide linkage and exemplary internucleoside cleavable sites for use in the oligonucleotide composition of the present invention.

The following terms, as used herein, have the meanings as indicated:

An "immobilization attachment site" is a site within an oligonucleotide primer for binding to a solid support material either directly or through an intervening spacer arm. The immobilization attachment site is located at the 5' end or 5' relative to the cleavable site and may require chemical modification prior to binding to the solid support. The immobilization attachment site may be attached to the solid support by either chemical or enzymatic means. Upon attachment of the immobilization attachment site to a solid support, the resulting immobilization linkage is one which remains stable under the conditions employed for cleaving the cleavable site and does not inhibit base pair hybridization nor block the ability to extend the primer from its 3' end.

"Cleavable site" as used herein is a reactive moiety typically (i) located at or within about five nucleotides from the 3' end of a primer, and (ii) selectively cleavable by appropriate non-enzymatic means including chemical, thermal, or photolytic, to enable release of primer extension products that typically contain none or a relatively small number of base pairs of the modified primer. Cleavable site refers both to the selectively cleavable functional group as described above and also to protected forms thereof. The cleavable site may, for example, be (i) located along the polymer backbone (i.e., a modified 3'-5' internucleotide linkage in place of one of the phosphodiester groups), (ii) as a substituent on or replacement of one of the bases or sugars of the oligonucleotide primer, or (iii) as the 3' terminal residue (e.g., a ribonucleotide at the 3' end of the oligodeoxyribonucleotide primer). The cleavable site is stable under standard solid phase DNA synthesis conditions, during primer immobilization, hybridization, primer extension, and washing conditions.

"Extension segment" refers to the product resulting from in vitro enzymatic extension at the 3' end of a primer, excluding the portion of nucleotides originally present in the primer prior to extension.

As used herein, "read length" refers to the number of nucleotides of a given target sequence for which new analytical data (e.g., sizing, quantification, sequencing) can be obtained. New data refers to fragment information for primer extension products which excludes data derived from portions of the target DNA complementary to the primer(s) employed (e.g., regions for which sequence information is already known).

Read length is typically method dependent (i.e., a function of the detection method being employed). In some analytical methods size resolution may have an essentially finite upper limit, e.g., up to nucleotides. One advantage of the present invention is the ability to improve the amount of new or useful information about a target DNA sequence that can be obtained from a primer extension product, when the products are analyzed using such a method.

For example, using the modified primers of the present invention, the read length of an exemplary extension segment would be determined as follows. A modified primer composed of 18 nucleotides complementary to a DNA target and having a cleavable linkage between nucleotides 17 and 18 (e.g., the cleavable site is within one nucleotide from the 3' end of the primer) is first annealed to the target strand, extended enzymatically (e.g., with a polymerase or ligase), and the resulting primer extension product (subsequent to immobilization) is cleaved at the cleavable site to produce an extension segment containing only one nucleotide derived from the primer. In carrying out sizing of the extension products, the read length is equal to the total number of nucleotides detected (X) minus the one nucleotide derived from the second region of the primer, or X-1.

In contrast, prior to cleavage at the cleavable site, the product composed of the primer and the same set of extension segments would have a read length of X-18, where 18 equals the number of bases in the primer. Thus the amount of new or useful sequencing or size information for primer extension products obtained using the modified primers of the present invention is improved.

II. OLIGONUCLEOTIDE COMPOSITION: SYNTHESIS OF MODIFIED PRIMERS

The oligonucleotide primers of the present invention (i) are designed for attachment to a solid support in a manner that does not block the ability to extend the primer from its 3' end, and (ii) incorporate a cleavable moiety so that a 3' portion of the primer (linked to an extension segment) can be released from an immobilized 5' portion. In the modified primer of the invention, the immobilization attachment site is generally separated from the cleavable site by at least three nucleotides. Upon selective cleavage of the cleavable site, a large portion of the primer fragment remains affixed to the solid support. This enables the release of primer extension products that contain about five or fewer base pairs of the primer sequence, to extend the useful size analysis range (e.g., increased read lengths). For sequencing applications, the modified primers can also provide more useful sequence information per fragment than extension products containing the entire primer.

Exemplary oligonucleotide sequences for use as primers or probes in the oligonucleotide composition of the present invention typically have lengths ranging from about eight to thirty nucleotides, preferably between about ten and twenty five nucleotides. Typically, the oligonucleotide sequences are complementary to a site upstream, relative to the 5' end, of the target sequence of interest, based on known sequence information for the target molecule. The oligonucleotide sequence may additionally contain a label in the releasable primer fragment (e.g., the second region), such as a radioactive or fluorescent tag, depending upon the method of sequence analysis employed.

Figure 5A:
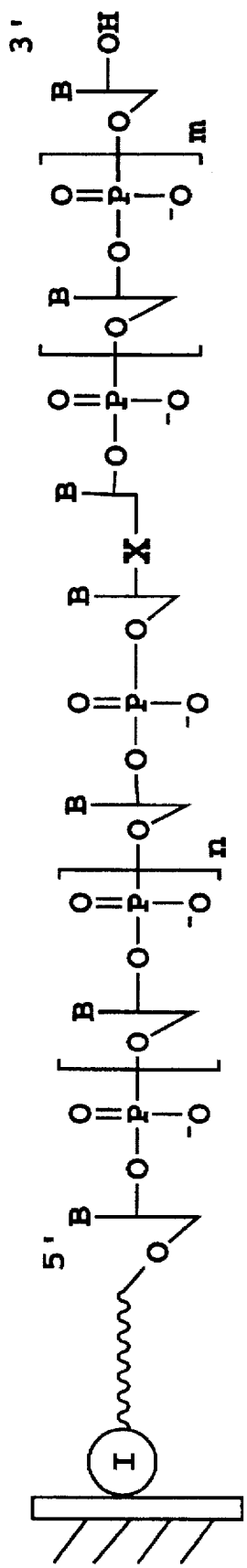
FIG. 5A–5E illustrate four alternate embodiments of an immobilized clearable primer in accordance with the invention.

The modified primers of the present invention, having a 5' end and a 3' end, are generally composed of two separate nucleotide regions. In one embodiment of the invention as illustrated in FIG. 5A, the two regions are connected by a cleavable site, as indicated by "X". The heterocyclic bases, adenine, thymine, guanine, and cytosine are commonly indicated in the figures by the symbol "B". The first region, containing the 5' end of the primer, contains an immobilization attachment site, "I", for attachment to a solid support. In the embodiment shown in FIG. 5A, the modified primer is in immobilized form. The immobilization site may optionally be separated from the 5' end of the primer by a spacer arm, as indicated. Spacer arms for use in the present invention are generally six or more atoms in length.

The number of nucleotides in the first region will vary, but typically will be at least about three nucleotides. In a preferred embodiment, the first primer region contains a significant portion of the nucleotides (e.g., typically from about 3-20 nucleotides) composing the modified primer. As shown, the cleavable linkage, "X", is a 3'-5'-internucleotide cleavable site which connects the first region to the second region. The second region, which contains the 3' end of the primer, is composed of as few nucleotides as is feasible, although the number will vary depending on the primer employed. Preferably, the second region contains from zero to five nucleotides and the total number of nucleotides in the modified primer will be between about eight and thirty, and preferably between ten and twenty five. The 3' end of the modified primer serves as a priming site for enzymatic extension.

Figure 5B:
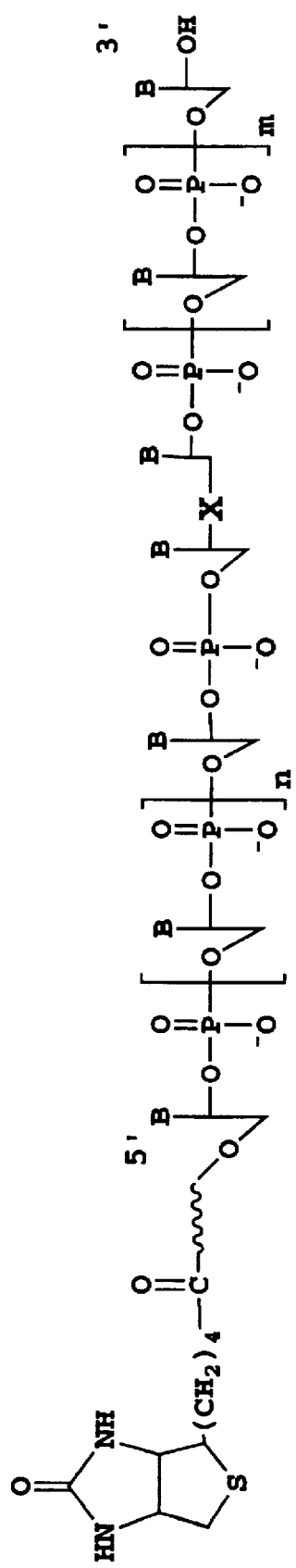

FIG. 5B illustrates an alternate embodiment of the present invention in which a biotin molecule is connected to the 5' end of a modified primer. The biotin is attached to the 5' end of the primer through an extended spacer arm which serves to reduce steric hindrance. Biotin, a relatively small vitamin molecule that binds with high affinity to both avidin and streptavidin, is one exemplary immobilization attachment site for use in the present invention. Biotinylated primers are available from commercial sources or may be synthesized by methods commonly employed in the art, typically utilizing a functionalized biotin reagent containing a reactive group suitable for coupling. As in FIG. 5A above, an internucleotide cleavable linkage separates the two regions of the modified primer. The second region contains a 3' end suitable for enzymatic extension, which may take place either prior to or after immobilization to a solid support.

Figure 5C:
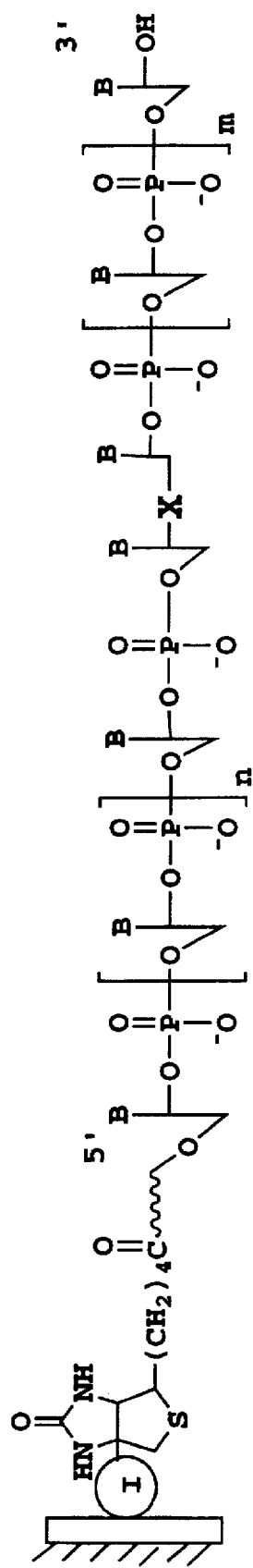

FIG. 5C illustrates capture of the modified primer of FIG. 5B prior to enzymatic extension on an avidin-functionalized solid support. In this embodiment of the invention, the modified primer is immobilized via a high affinity interaction between avidin and biotin, as indicated by "I".

Figures 5D, 5E:
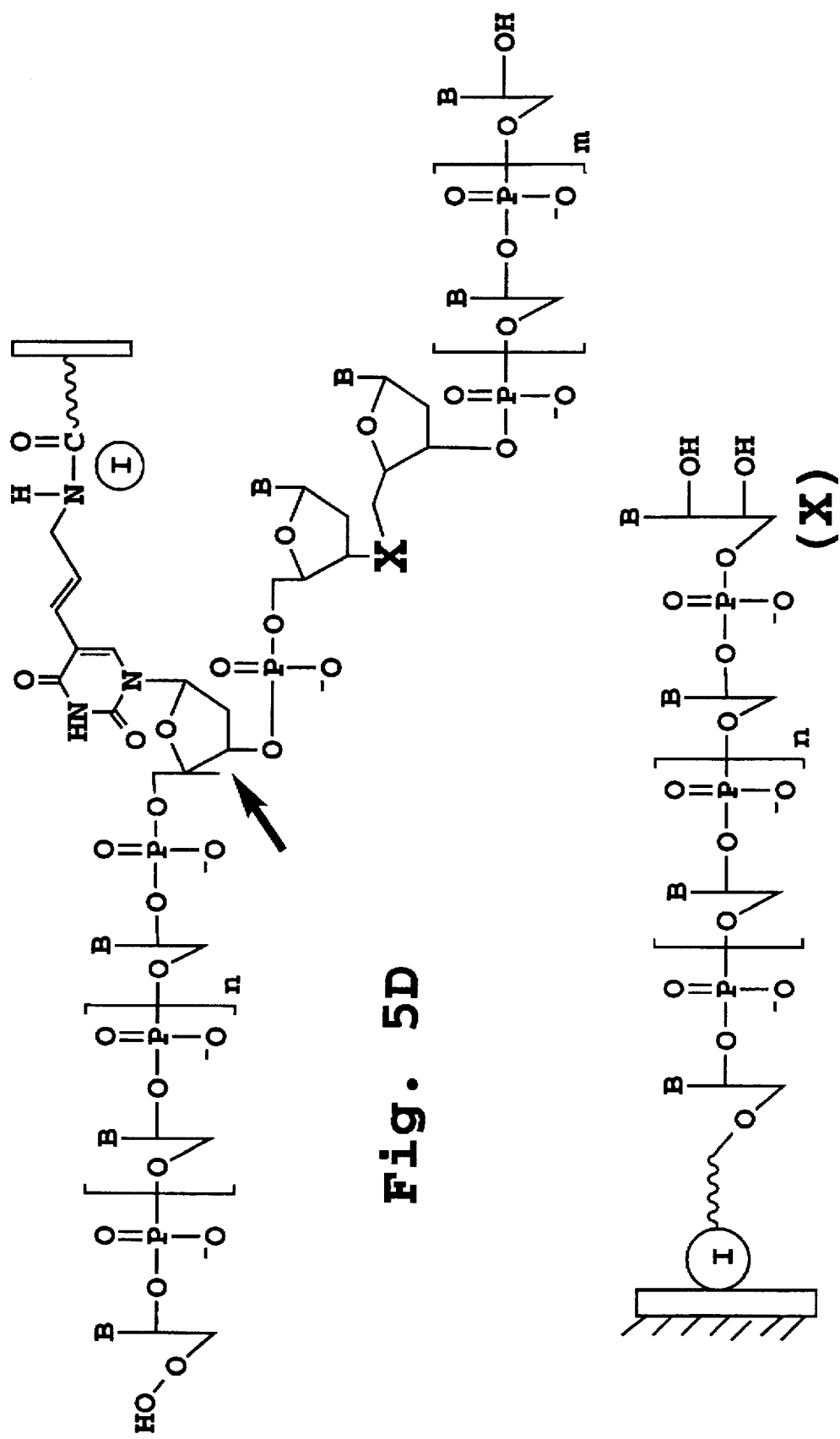

FIG. 5D illustrates an alternate embodiment of the invention in which the modified primer is attached to a solid support through an immobilization attachment site present as a substituent on one of the heterocyclic bases. As shown in FIG. 5D, the site for immobilization is an amino residue substituted at the 5 position of a uracil (Dattagupta, 1989), and more specifically, is a 5-allylamino substituent. The amino group may be in protected form (e.g., trifluoroacetamido) prior to attachment to the solid support. As indicated, immobilization to the solid support is through an amide linkage, although any of a number of immobilization attachment linkages may be used, as will be described in more detail below. Coupling of the amino residue to a solid support is generally carried out by using an activated support material, such as an N-hydroxysuccinimide (NHS) ester functionalized support.

In the embodiment shown in FIG. 5D, the immobilized primer is in a branched or "T"-configuration. As in the above embodiments, the modified primer contains two regions separated by a cleavable linkage indicated by "X". The first region contains the 5' end of the primer and an immobilization attachment site as described above. Referring to the design of a "T"-configured primer as shown in FIG. 5D, generally, a large portion of the nucleotides composing the modified primer and required for sequence specific target binding are located 5' of the "central" deoxyribose, indicated by an arrow. The second region contains the 3' end of the primer which serves as a priming site for enzymatic extension. In the exemplary modified primer shown, following hybridization to a target DNA, and enzymatic extension followed by denaturing and washing, selective cleavage of the cleavable site "X" releases the second region of the modified primer along with the extension product (e.g., the extension segment), while the first region containing a large portion of the nucleotides required for sequence specific target binding remains immobilized.

FIG. 5E illustrates an exemplary modified primer containing a terminal cleavage site, as indicated by an (X). In this embodiment of the invention, the cleavable linkage is represented by a ribose moiety, although any of a number of terminal cleavable sites may be employed. As shown, the modified primer is in immobilized form and contains an immobilization attachment site 5' of the cleavable site. The first region contains the immobilization attachment site and the portion of the primer up to, but not including the ribose. The ribose, or, alternatively, the cleavable site, represents the second primer region and also serves as a priming site for enzymatic extension.

In all of the exemplary embodiments described above, cleavage of the cleavable site results in the release of newly synthesized primer extension products containing little or none of the nucleotide bases originally present in the modified primer.

A. INTRODUCTION OF THE CLEAVABLE SITES

The cleavable site is typically introduced into an oligonucleotide probe by using one of following synthetic approaches. Depending upon the choice of cleavable site to be introduced, either a functionalized nucleoside or a modified nucleoside dimer is first prepared, and then selectively introduced into a growing oligonucleotide fragment during the course of primer synthesis. The primer containing the cleavable site may be prepared using solution synthesis, or preferably, employing automated solid phase synthesis conditions using a DNA synthesizer.

In forming a modified dimer, two suitably protected nucleosides are coupled to each other to form a modified 3'-5'-internucleoside linkage. The dimer containing the cleavable site (or a protected form thereof) is then incorporated into the oligonucleotide primer during synthesis to form a modified oligonucleotide containing a cleavable site. The cleavable site is chemically cleavable under select conditions but is stable under standard solid phase DNA synthesis, solid support attachment, primer extension and hybridization conditions.

Alternatively, functionalization is carried out on a single nucleoside to introduce a reactive group suitable for forming a cleavable site upon reaction with a second nucleoside molecule or during primer synthesis.

Although functionalization may take place at sites within the base or the sugar of the nucleoside, typically, modification will be carried out to result in an oligonucleotide primer containing a specific cleavable site in place of one of the phosphodiester linkages of the resulting polymer. Preferred non-internucleotide locations for modification or introduction of a cleavable site include C(5) of uracil and N(4) of cytosine, as these two base sites are readily chemically manipulated without preventing base pairing.

Figure 1B:
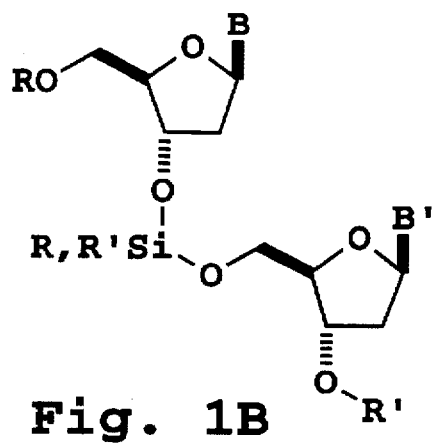
Figure 1C:
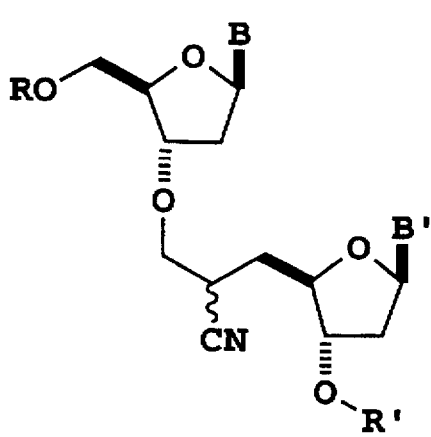
Figure 1D:
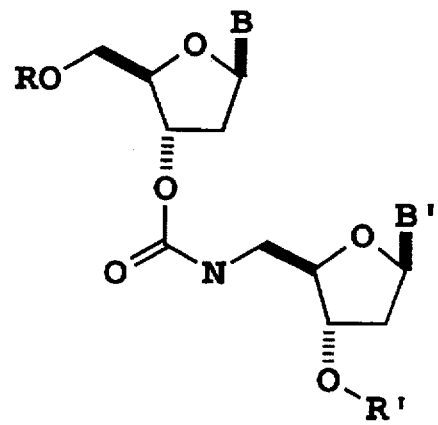
Figure 1E:
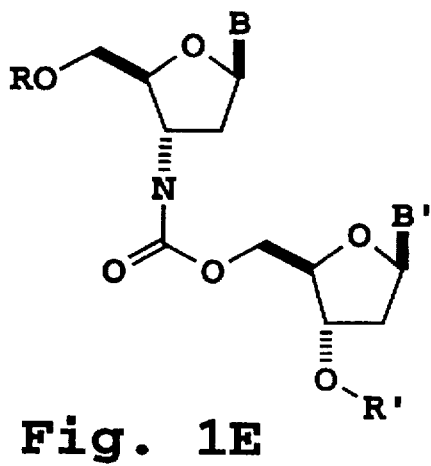
Figure 1F:
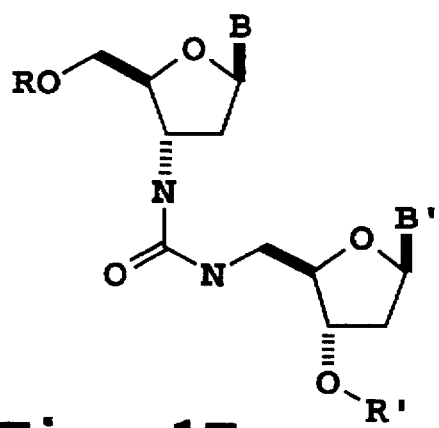
Figure 1G:
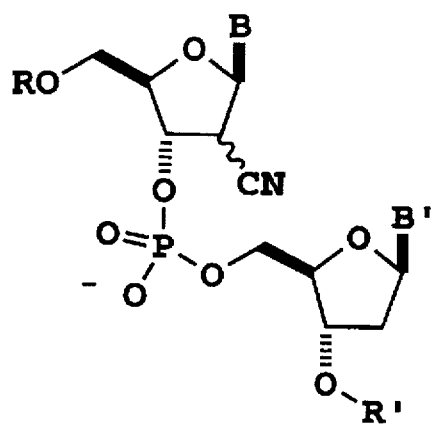
Figure 1H:
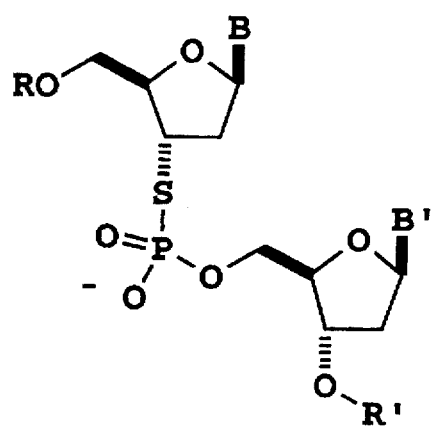
Figure 1I:
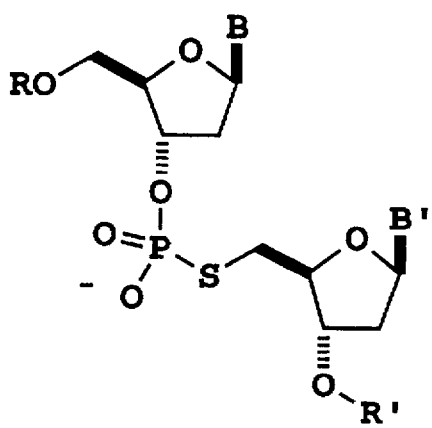
Figure 1J:
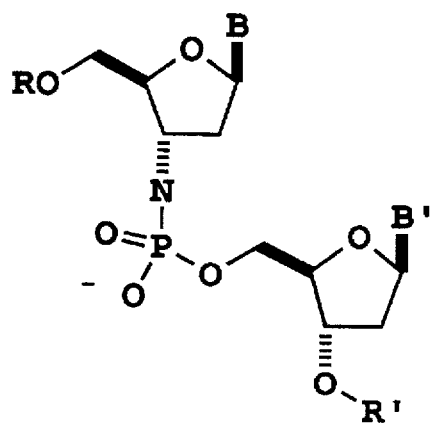
Figure 1K:
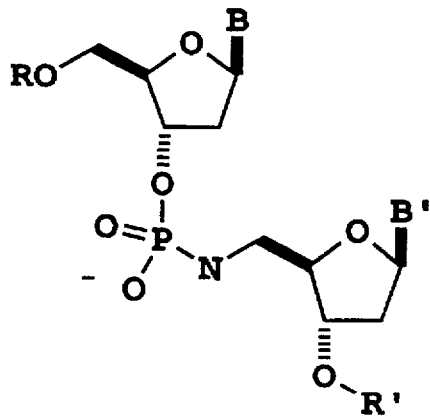
Figure 1L:
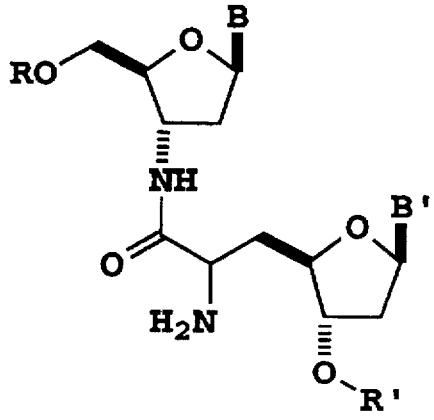
Figure 1M:
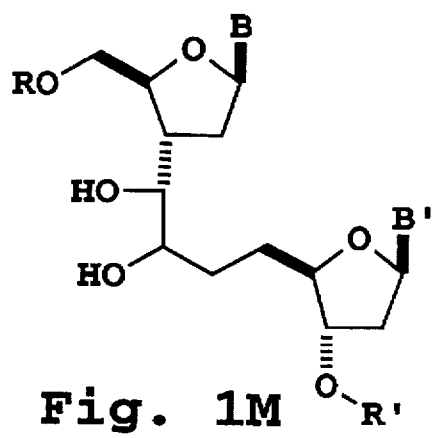
Figure 1N:
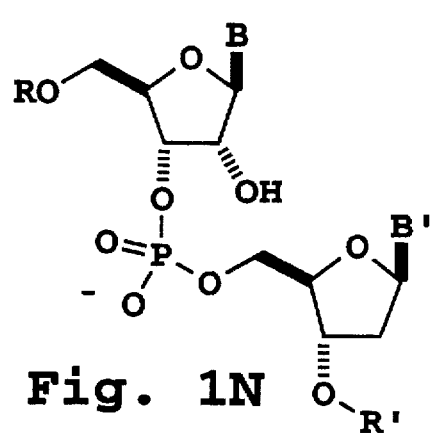
Figure 1O:
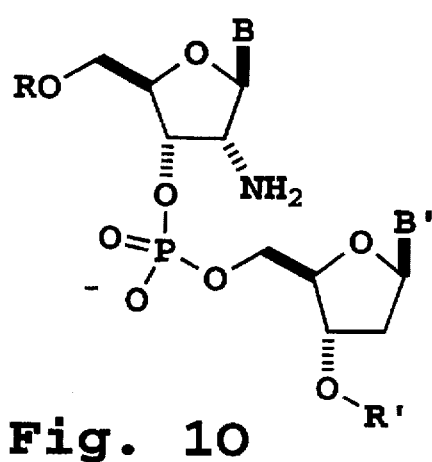
Figure 1P:
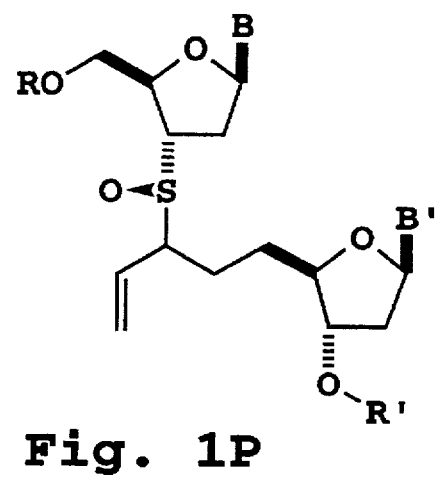
Figure 1Q:
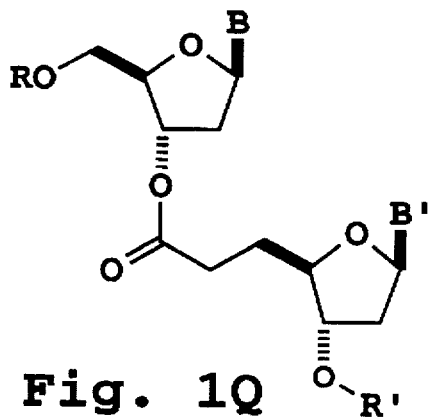
Figure 1R:
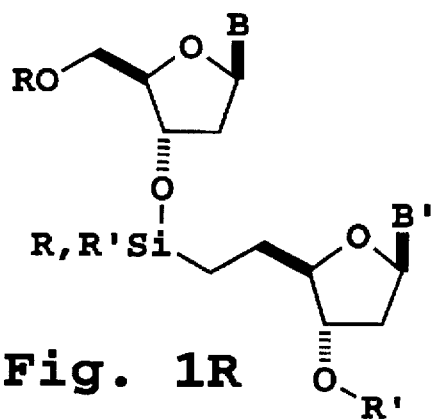
Figure 1S:
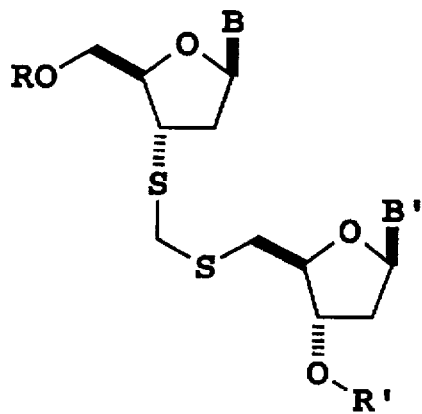
Figure 1T:
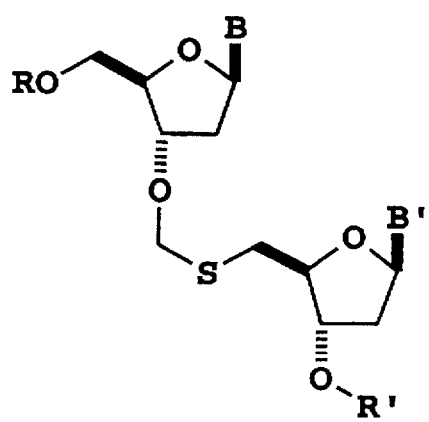
Figure 1U:
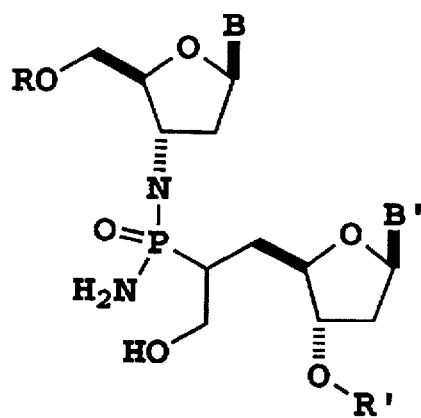
Figure 1V:
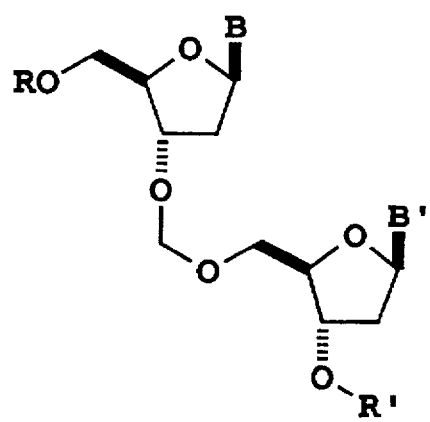
Figure 1W:
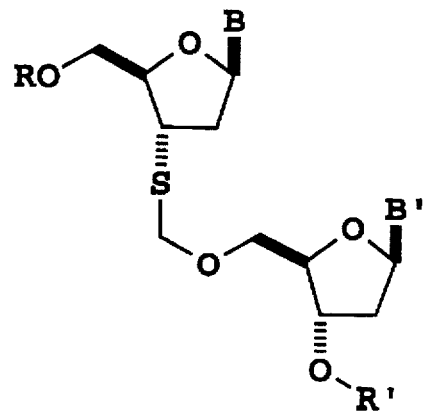

A number of exemplary internucleoside cleavable sites for use in the oligonucleotide composition of the present invention are illustrated in FIGS. 1B–1W. FIG. 1A is an illustration of an unmodified, native 3,-5,-phosphodiester linkage. A clearable site or linkage for use in the invention is one which may be introduced at a specific position within the oligonucleotide sequence, preferably at or within about five nucleotides from the 3' end of the primer, and is selectively cleaved under conditions which do not permit cleavage of the immobilization attachment site. In one preferred embodiment, the cleavable site is located at the 3' end of the primer. The cleavable linkage should also be one that is chemically accessible.

Chemically cleavable internucleotide linkages for use in the present invention include but are not limited to the following, as illustrated in FIGS. 1B–1W, respectively: dialkoxysilane, FIG. 1B; β-cyano ether, FIG. 1C; 5'-deoxy-5'-aminocarbamate, FIG. 1D; 3'deoxy-3'-aminocarbamate, FIG. 1E; urea, FIG. 1F; 2'cyano-3', 5'-phosphodiester, FIG. 1G; 3'-(S)-phosphorothioate, FIG. 1H; 5'-(S)-phosphorothioate, FIG. 1I; 3'-(N)-phosphoramidate, FIG. 1J; 5'-(N)-phosphoramidate, FIG. 1K; α-amino amide, FIG. 1L; vicinal diol, FIG. 1M; ribonucleoside insertion, FIG. 1N; 2'-amino-3',5'-phosphodiester, FIG. 10; allylic sulfoxide, FIG. 1P; ester, FIG. 1Q; silyl ether, FIG. 1R; dithioacetal, FIG. 1S; 5'-thio-furmal, FIG. 1T; α-hydroxymethyl-phosphonic bisamide, FIG. 1U; acetal, FIG. 1V; and 3'-thio-furmal, FIG. 1W. Other chemically cleavable linkages include methylphosphonate and phosphotriester. Cleavable linkages suitable for non-chemical cleavage methods such as photolysis or thermolysis include nitrobenzyl ether (NBE), cis-syn thymidine dimer (Nadji, et al., 1992), and cyclohexene.

Nucleoside dimers containing the cleavable linkages illustrated in FIGS. 1B–1W are synthesized using standard nucleic acid chemistry known to one of skill in the art (Hobbs, 1990; Townsend, et al., 1986). Alternatively, one may directly synthesize a modified nucleoside containing either a 5'- or 3'-reactive group (or protected form thereof) for use in standard solid phase synthesis to introduce the desired cleavable linkage. 2'-Functionalized nucleosides are typically prepared from the corresponding ribonucleoside starting materials. An internucleotide β-cyano ether linkage, as shown in FIG. 1C, may be formed by reaction of a suitably protected nucleoside with a 5'-(2-cyanoallyl) functionalized 3'-phosphoramidite. Selective cleavage is effected by a β-elimination reaction upon treatment with base, promoted by the presence of the β-cyano substituent. A nucleoside dimer containing a 3'-(O)-carbamate internucleoside bond is prepared by any of a number of synthetic approaches including reaction between the corresponding 3'-acyl chloride and a 5'-amino-modified nucleoside. Alternatively, a 3'-modified isocyanate nucleoside is prepared and subsequently reacted with the 5'-hydroxyl of a suitably protected nucleoside. A nucleoside dimer containing a 5'-(O)-carbamate cleavable linkage is prepared from the imidazoyl carbamate precursor.

Oligonucleosides containing methyl phosphonate linkages are prepared using solid support based synthesis with phosphonamidite reagents used in place of the standard phosphoramidites (Agrawal and Goodchild, 1987). Phosphotriesters are somewhat labile under basic deblocking conditions, however, this cleavable group may be introduced into an oligonucleotide backbone by using mild reaction conditions or more labile amine protecting groups (Miller, et al., 1971). Methanol or ethanol in the presence of tosyl chloride is used to esterify the internucleoside phosphate group (Moody, et al., 1989); methyl methanesulfonate may also be used as a methylating agent (Koole, et al., 1987).

Preferred cleavable sites for use in the modified oligonucleotide composition include dialkoxysilane, ribose, 3'-and 5'-phosphoramidate, and 3'-and 5'-phosphorothioate.

In one embodiment of the present invention, the cleavable site contained in the modified oligonucleotide primer is dialkoxysilane (Ogilvie, et al., 1986; Seliger, et al., 1987; Cormier, et al., 1988). Synthesis of a primer containing a dialkoxysilane internucleotide linkage is described in Example 1A. Although the preparation of a diisopropylsilyl-linked dinucleoside is described in Example 1A, alkyl groups for use as substituents on silicon are not limited to isopropyl and may be either straight chain or branched alkyl groups. Further, the two alkyl substituents on silicon may be identical, as in the case of diisopropylsilyl, or may be different. A variety of dialkylsilylating reagents are available from Petrarch Systems, Bertram, PA.

In the synthetic approach outlined in Example 1A, a reactive 3'-O-silyl ether intermediate is first prepared, followed by formation of a nucleoside dimer containing a 3'-5'-diisopropylsilyl internucleoside bridging group. Formation of a the 3'-protected silanol intermediate is carried out by reacting a 5'-O-dimethoxytrityl(DMT) -protected nucleoside, such as 5'-O-DMT-thymidine or the 5'-O-N-protected nucleosides N6-benzoyl-2'-deoxy-5'-O-(DMT) adenosine, N4-benzoyl-2'-deoxy-5'-0-(DMT)cytidine, or N2-isobutryl-2'-deoxy-5'-O-(DMT)guanosine, with an O-protected silane reagent.

In Example 1A, the protected nucleoside is treated with the reactive silane, bis(trifluoromethanesulfonyl) diisopropylsilane, in the presence of the sterically hindered base, 2,6-di-tert-butyl-4-methylpyridine, to promote formation of the desired 3'-O-diisopropylsilyl triflate intermediate. Use of a bulky base such as the tri-substituted pyridine reagent helps to prevent formation of the undesired symmetrical nucleoside dimer formed by condensation of unreacted nucleoside with the triflate intermediate (Saha, et al., 1993).

Following introduction of the desired 3'-O-silyl ether group, the 3'-O-diisopropylsilyl triflate intermediate is reacted with unprotected nucleoside to form the desired nucleoside dimer containing a 3'(O),5'(O)-dialkoxysilane cleavable site. The protected dimer may then be further functionalized, for instance, by conversion of the 3'-hydroxyl to the corresponding 2-cyanoethyl-N,N-diisopropylphosphoramidite for use in automated solid phase synthesis utilizing standard phosphoramidite chemistry to provide the desired primer sequence. Selective cleavage of the dialkoxysilane site is effected by treatment with fluoride ion (Corey and Snider, 1972)

Another preferred selectively cleavable functionality for use in the invention is phosphorothioate. The preparation of primers containing a 3'(S)-phosphorothioate or a 5'(S)- phosphorothioate internucleotide linkage is described in Examples 1B and 1C, respectively. In accordance with the modified oligonucleotide composition of the invention, the phosphorothioate internucleotide linkage is selectively cleaved under mild oxidative conditions (Cosstick, et al., 1989).

In one synthetic approach for preparing primers containing a 3'(S)-phosphorothioate cleavable site as described in Example 1B, a protected 3'-thio-substituted nucleoside starting material, such as 5-O-MMT-3'-S-benzoyl-3'-thymidine (Cosstick, et al., 1988), is first deprotected by treatment with base to form the debenzoylated thiol, 5'-O-MMT-3'-thiothymidine, followed by conversion to the corresponding reactive thiophosphoramidite by reaction with 2-cyanoethyl-N,N-diisopropylaminophosphormonochloridite. The reactive thiophosphoramidite is coupled to a second nucleoside molecule to form the corresponding thiophosphite dimer, followed by oxidation of the phosphorus center to form the fully protected 3'-(S)-phosphorothioate-linked dimer.

In order to promote coupling of the thiophosphoramidate to a second nucleoside molecule such as 3'-O-acetylthymidine and prevent undesired self-condensation side reactions, an acidic activating agent, 5-(para-nitrophenyl)tetrazole, is used. The thiophosphite dimer is oxidized with a suitable oxidant such as tetrabutylammonium oxone or tetrabutylammonium periodate to form the fully protected (P-(O)-2-cyanoethyl-3'-acetyl) dimer containing a protected form of the desired internucleoside linkage. Deprotection is readily carried out under standard conditions as described in Example 1B. As discussed above, the nucleoside dimer, containing a 3'-(S)phosphorothioate cleavable linkage may be readily incorporated into an oligonucleotide primer using standard solid phase phosphoramidite chemistry.

Alternatively, one may use the reactive thiophosphoramidite directly to introduce the desired 3'-(S)-phosphorothioate linkage into an oligonucleotide primer during solid phase synthesis. For introduction of a functionalized nucleoside containing a 3'-(S)-thiophosphoramidite during solid phase synthesis on controlled pore glass, during the coupling cycle for introducing the thio-modified nucleoside, the thio-modified nucleoside, dissolved in acetonitrile saturated with 5-(para-nitrophenyl)tetrazole, is injected into the column containing the solid support, and the coupling efficiency is monitored by release of trityl cations.

After preparing the desired immobilized, cleavable primer in accordance with the present invention, and carrying out the desired hybridization and primer extension reactions, the phosphorothioate internucleotide site is cleaved by treatment with a mild oxidizing agent such as aqueous silver nitrate.

Preparation of the corresponding 5'-(S)phosphorothioate modified oligonucleotide is carried out in a somewhat different fashion than that described above for the 3'-(S)-phosphorothioate and is described in detail in Example 1(C). The approach makes use of a key 5-thio-modified nucleoside intermediate for incorporation of the desired 5'-(S)-phosphorothioate cleavable linkage during solid phase oligonucleotide synthesis (Mag, et al., 1991; Sproat, et al., 1987).

Synthesis of the nucleoside building block containing a protected 5'-thio group is carried out by first preparing the 5'-tosylate of thymidine by treatment with tosyl chloride, followed by conversion of the 5'-tosylate to 5'-(S-trityl)-mercapto-5'-deoxythymidine. 5'-Tosyl-thymidine is converted to 5'-(S-trityl)-mercapto-5'-deoxythymidine by treatment with a five-fold excess of sodium tritylthiolate, which is prepared in-situ by deprotonation of tritylmercaptan with sodium hydroxide. In the above synthetic step, a sulfur atom is introduced into the 5'-position of a nucleoside, forming the S-trityl precursor of the desired key intermediate. Subsequent phosphitylation at the 3'-position with 2-cyanoethoxy-bis-(N,N-diisopropylamino)phosphine in the presence of tetrazole results in the desired functionalized nucleoside, 5'-(S-trityl)-mercapto-5'-deoxythymidine-3'-O-(2-cyanoethyl-N,N-diisopropylamino)phosphite.

The 5'-S-protected nucleoside intermediate is introduced into an oligonucleotide primer using standard solid-phase phosphoramidite chemistry by first coupling it to a deprotected polymer-bound oligonucleotide. The phosphite linkage is then oxidized with aqueous $I_2$, and the S-trityl group is cleaved with silver nitrate and reduced with dithiothreitol to form a reactive thiol. The thiol is then coupled to a 2'-deoxynucleoside-3'-phosphoramidite, followed by oxidation of the thiophosphite linkage to yield the desired 5'-phosphorothioate cleavable site.

Selective cleavage of the phosphorothioate site may also be effected by treatment with an aqueous solution of either silver nitrate.($AgNO_3$) or mercuric chloride ($HgCl_2$).

Another functional group for use as a cleavable site in the modified oligonucleotide composition of the invention is phosphoramidate. Oligonucleotides bearing phosphoramidate internucleotide linkages can be prepared chemically by standard, solid phase DNA synthesis (Bannwarth, 1988). Preparation of primers containing a 5'(N)-phosphoramidate internucleotide linkage is described in Example 1D. In the synthetic approach described in Example 1D, a 5'-amino-modified nucleoside is either purchased commercially or synthesized by conversion of the 5'-hydroxyl group to the corresponding azide, followed by reduction over a palladium/carbon catalyst (Yamamoto, et al., 1980).

The 5'-amino group is then protected by treatment with 4-methoxytritylchloride, followed by reaction with bis (diisopropylammonium)tetrazolide and (2-cyanoethoxy)bis (diisopropylamino)phosphine to form the corresponding 3'-(2-cyanoethyl)-N,N-diisopropylphosphoramidite-functionalized nucleoside. This reactive nucleoside, containing a 5'-protected amino function, is then selectively introduced into an oligonucleotide fragment during standard solid phase DNA synthesis utilizing phosphoramidite chemistry, to form the desired 5'-phosphoramidate bond. Selective cleavage of the phosphoramidate bond is carried out under mild acidic conditions, such as by treatment with 80% acetic acid. Phosphoramidate linkages are more labile in the ribo series than in the deoxyribo series (Tomasz, et al., 1981).

Another functional group for use as a cleavable site in the present oligonucleotide composition is ribose. Modified primers containing a cleavable ribose are described in Examples 3–5. Ribose, containing suitable 0-protecting groups, is selectively introduced into a growing oligomer fragment during automated solid phase synthesis using standard phosphoramidite chemistry. Selective cleavage is carried out by treatment with dilute ammonium hydroxide, as described in Examples 3 and 5.

B. ATTACHMENT TO SOLID SUPPORT

The oligonucleotide primers of the present invention (i) are designed for attachment to a solid support in a manner that does not block the ability to extend the primer from its 3' end, and (ii) incorporate a cleavable moiety so that a 3' portion of the primer (linked to an extension product) can be released from an immobilized 5' portion.

In the modified primer of the invention, the immobilization attachment site is typically separated from the cleavable site by at least three nucleotides. Upon selective cleavage of the cleavable site, a large portion of the primer fragment remains affixed to the solid support. This enables the release of primer extension products that typically contain about five or fewer base pairs of the primer sequence, to provide more useful sequence information per fragment than extension products containing the entire primer.

The modified primers of the present invention may, for example, be used for detecting a genetic disorder for which the nucleotide sequence of both the wild type and mutant alleles are known. A modified primer for this purpose will have a 5' end and a 3' end and contain from about 8–30 base pairs complementary to the gene sequence upstream from the known mutation site. Preferably, the 3' end of the primer is complementary to a site upstream from the known mutation region by at least about ten base pairs, to provide verifying sequence information on either side of the mutation region.

In accordance with the invention, the modified primer also contains (i) an immobilization site for attachment to a solid support and (ii) a cleavable site. The immobilization site is located 5' of the cleavable site which is preferably located at or within about five base pairs from the 3' end of the primer.

The modified primer is then used as a probe to distinguish the presence of DNA containing the mutant sequence of interest. The primer is (i) hybridized to an unknown, single stranded, target DNA sequence utilizing conditions under which both the mutant and the normal sequences will anneal stably to the primer, and (ii) enzymatically extended. Primer immobilization may optionally take place either before or after chain extension. Following chain extension and release of the immobilized primer extension products by selective cleavage of the cleavable linkage, the primer extension products are analyzed to determine the sequence across the known mutation region and identification of the genetic disorder, if present.

Figure 6A:
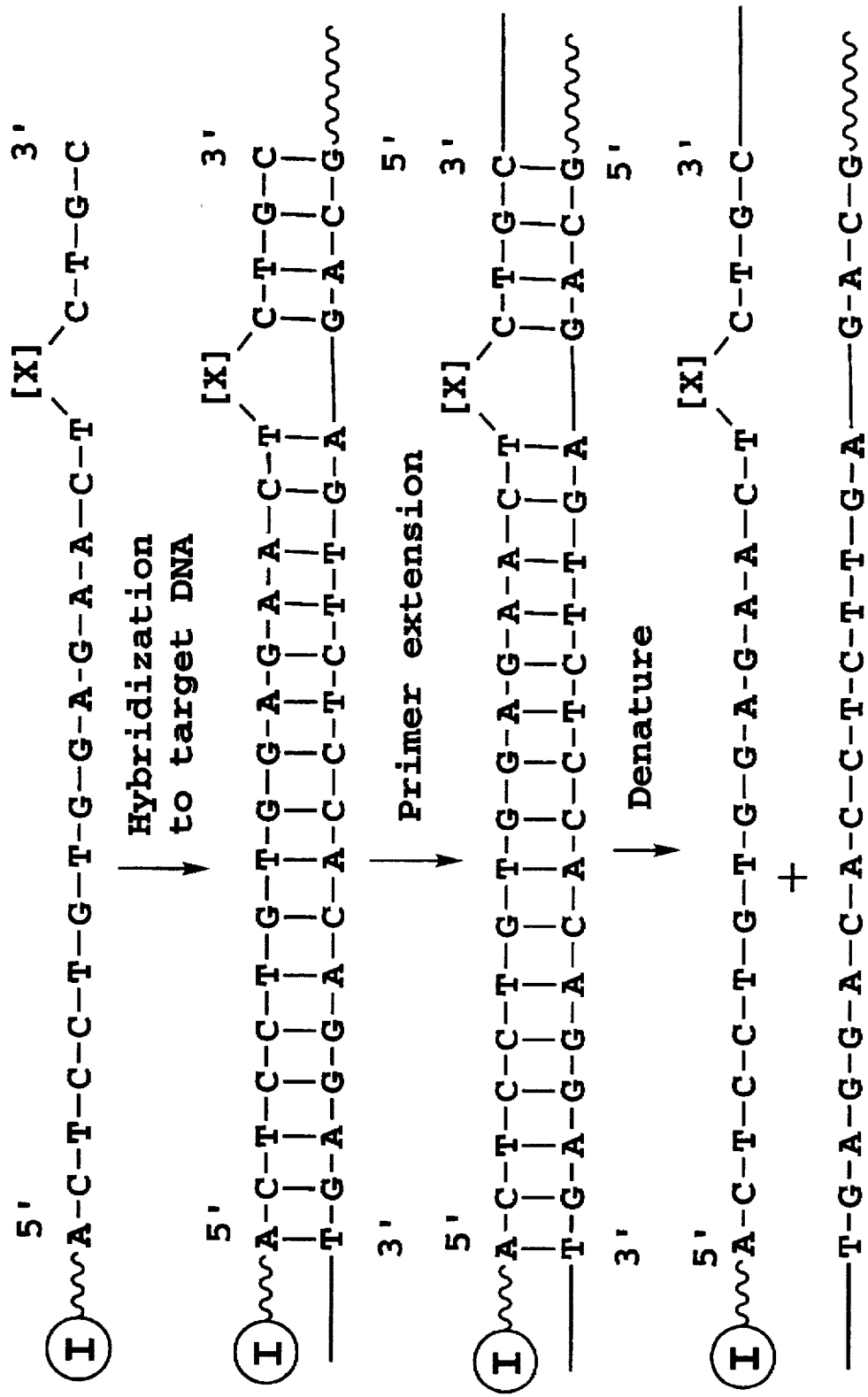
FIGS. 6A and 6B illustrate an exemplary method of determining the sequence of a target DNA molecule using the immobilizable, cleavable primers of the present invention.
Figure 6B:
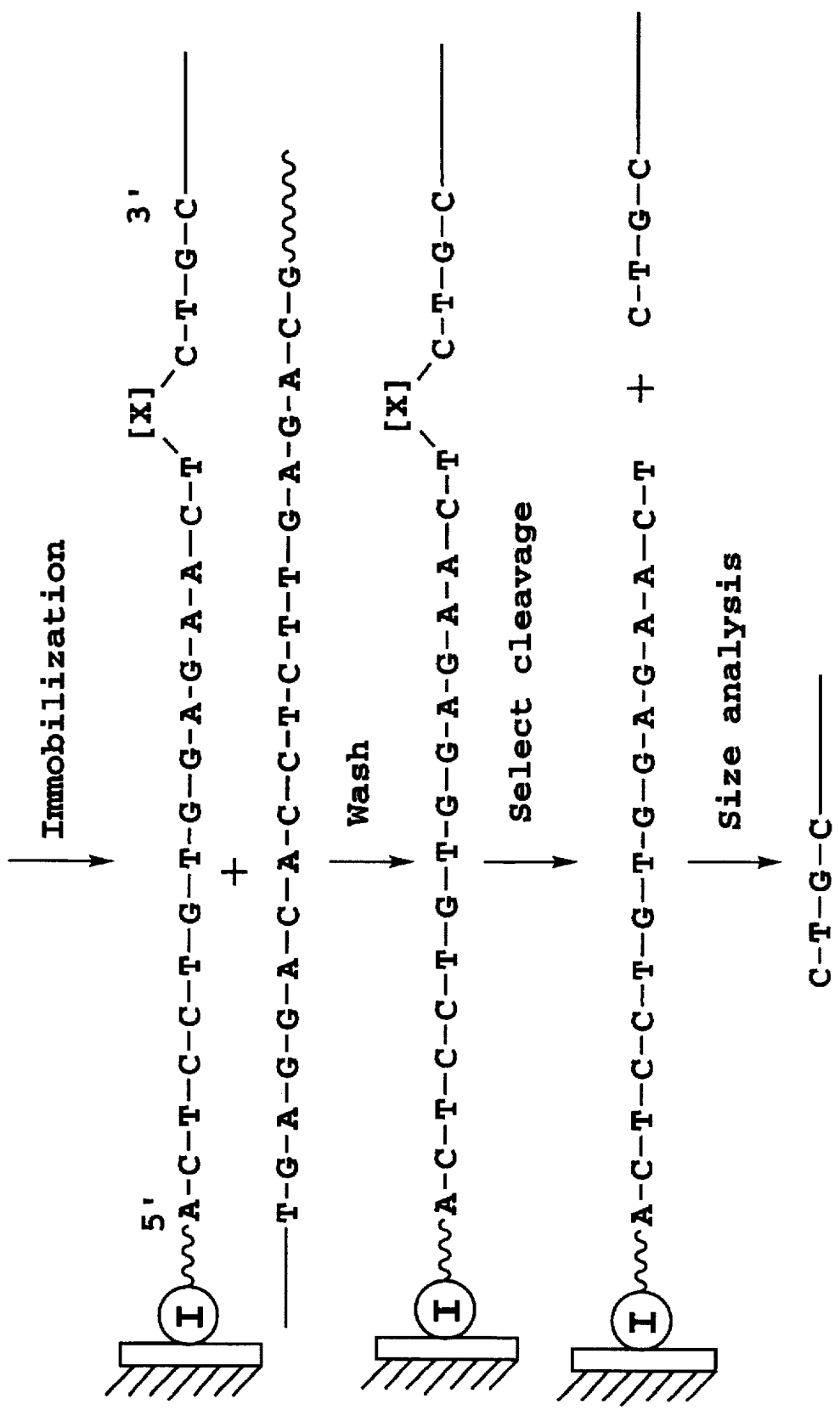

An exemplary modified primer containing 20 deoxynucleotide residues and specific for its ability to detect a known genetic disorder is shown in FIGS. 6A and 6B. As indicated, the modified primer contains a first region containing an immobilization attachment site, "T", that is 5' of the cleavable site, "X", and consists of a total of 16 nucleotide residues. The second region contains the 3' end of the primer and contains 4 nucleotides (C-T-G-C). The cleavable linkage, X, connects the first and second regions.

In illustrating this aspect of the invention, the modified primer as shown in FIG. 6A (top) and having the sequence presented as SEQ ID NO:2, is first hybridized to a single stranded DNA target having the sequence presented as SEQ ID NO:3, as shown in FIG. 6A. Typically, the hybridization medium contains (i) denatured, unknown (target) DNA from a human or other biological source, (ii) the modified probe, and (iii) annealing buffer, such as 5× "SEQUENASE" Buffer (200 mM Tris-HCl pH 7.5, 100 mM $MgCl_2$, 250 mM NaCl) (United States Biochemical Corporation, Cleveland, Ohio). The annealing reaction is carried out by warming the above mixture to 65° C. for two minutes, and then allowing the mixture to cool slowly to room temperature over a period of about thirty minutes (Maniatis, et al., 1982; Ausubel, et al., 1989).

Following hybridization, the modified primer is extended on the single stranded template with deoxynucleotides and randomly terminated with dideoxynucleotides using DNA polymerase (e.g., "SEQUENASE" DNA Polymerase, Version 1.0 or 2.0) to initiate DNA synthesis (Primings, et al., 1980; Sanger, 1975). As indicated in FIG. 6A, extension occurs from the 3' end of the modified primer. The primer extension products are denatured from the target, typically using heat or a chemical denaturant such as formamide, to provide a mixture of both primer extension products and target DNA. (See for example "PROTOCOLS FOR DNA SEQUENCING WITH SEQUENASE T7 DNA POLYMERASE", Version 1.0 or 2.0, 4th ed., United States Biochemical, or "CIRCUMVENT Thermal Cycle Dideoxy DNA Sequencing Kit Instruction Manual", New England Biolabs, Inc., Beverly Mass).

As shown in FIG. 6B, the primer extension products are then bound to the solid support at the immobilization attachment site, although immobilization may optionally be carried out prior to enzymatic extension. By immobilizing the extended primers, the target DNA strands which remain free in solution are readily removed, along with excess reagents, ions, enzymes and the like, in a series of wash steps. Generally, the solid substrate is washed with large volumes of a wash solution (e.g., 10 mM TrisHCl, 1 mM EDTA; or pure water) at room temperature.

The solid particles, containing immobilized primer extension products and free of impurities, are then submitted to conditions effective to selectively cleave the cleavable site while maintaining the first primer region having the sequence presented as SEQ ID NO:4, affixed to the solid support as shown in FIG. 6B. As indicated in the particular embodiment illustrated in FIG. 6B, selective cleavage results in release of primer extension products containing only four nucleotides from the original modified primer. The supernatant containing the released extension segments is suitable for subsequent analysis.

Exemplary genetic disorders for detection using the modified primers of the present invention include sickle cell anemia and $\alpha_1$-antitrypsin deficiency (Watson, et al., 1992). As shown in FIG. 7A, sickle cell anemia results from a mutation that changes a glutamic acid residue (coded by the triplet GAG) for a valine residue (coded by GTG) at position 6 in the β-globin chain of hemoglobin. This base change (A to T) destroys the recognition sequence for a number of restriction enzymes, including MstII. A modified primer for detecting this disorder would typically contain a cleavable site as indicated in FIG. 7A, located about 2 nucleotides from the end of the primer and preferably about 10–20 nucleotides upstream from the known mutation site.

Also detectable using the modified primers of the present invention is α1-antitrypsin deficiency, a disorder characterized by uninhibited production of elastase, a protease which destroys the elastic fibers of the lung causing patients to suffer from pulmonary emphysema. The α1-antitrypsin gene has been cloned and as shown in FIG. 7B, the mutant gene (a fragment of which is presented by SEQ ID NO:7) corresponds to a single base change that leads to an amino acid substitution (glutamine to lysine) at residue 342 as indicated by SEQ ID NO:8

A portion of the wild α1-antitrypsin gene, as shown in FIG. 7B (top), is presented by SEQ ID NO. 5. A fragment of the protein produced in individuals having the wild type α1-antitrypsin gene is presented by SEQ ID NO:6. Other diseases for which the corresponding gene mutations have been identified and which may be detected using the modified primers of the present invention include Duchenne muscular dystrophy, factor X deficiency, hemophilia and phenylketonuria.

Immobilization simplifies purification of the primer extension products for subsequent analysis. As discussed above, undesirable enzymes, salts, reagents, and sequencing targets are washed away prior to selective cleavage of the extension product.

In immobilizing the modified primers of the present invention, the first region of the primer may be attached to the solid support material either prior to or after introduction of the cleavable site. Any of a number of methods commonly employed in the art may be utilized to immobilize an oligonucleotide on a solid support (Saiki, et al., 1989; Zhang, et al., 1991; Kremsky, et al., 1987; Van Ness, et al., 1991; Ghosh, et al., 1987; Gingeras, et al., 1987; Khrapko, et al., 1991). Solid support materials for use in the invention include cellulose, nitrocellulose, nylon membranes, controlled-pore glass beads, acrylamide gels, polystyrene matrices, activated dextran, avidin/streptavidin-coated polystyrene beads, agarose, polyethylene, functionalized plastic, glass, silicon, aluminum, steel, iron, copper, nickel and gold.

Some substrates may require functionalization prior to attachment of an oligonucleotide. Solid substrates that may require such surface modification include wafers of aluminum, steel, iron, copper, nickel, gold, and silicon. In one approach, the solid substrate material is functionalized by reaction with a coupling agent, such as a zircoaluminate.

Zircoaluminates generally contain both oxo and hydroxy bridges and are characterized by high thermal and hydrolytic stability. Such compounds, due to their highly metallic nature, are particularly reactive with metal surfaces such as the metallic solid supports described above. Bi-functional zircoaluminates containing a variety of organofunctional groups are commercially available (e.g., "MANCHEM" Zircoaluminates, Rhône-Poulenc Latex & Specialty Polymers, Cranbury, N.J.).

Upon attachment to a solid support, the oligonucleotide, typically DNA, should couple efficiently to the solid support material. Further, the immobilized DNA should be both stable upon immobilization and accessible for base hybridization and other potential derivatization reactions. The immobilization attachment site should remain stable under the conditions employed for selectively cleaving the cleavable site in the modified oligonucleotide composition of the invention.

Coupling of an oligonucleotide to a solid support may be carried out through a variety of immobilization attachment functional groups. Immobilization attachment sites for use in the present invention include those illustrated in FIGS. 2A–2M. Attachment of the support material to the oligonucleotide may occur by reaction between the reactive site on the support and a reactive site contained within the oligonucleotide or via an intervening linker or spacer molecule.

Figure 2A:
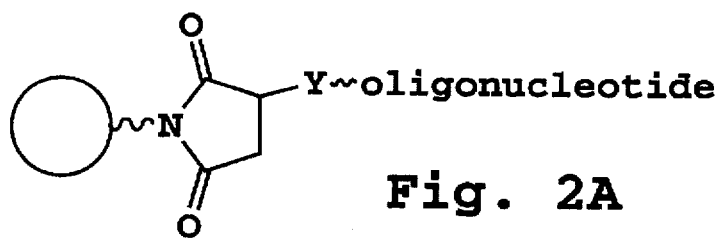
Figure 2B:
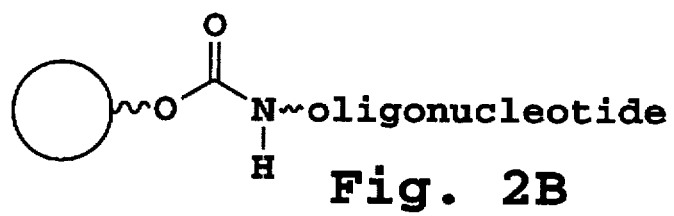
Figure 2C:
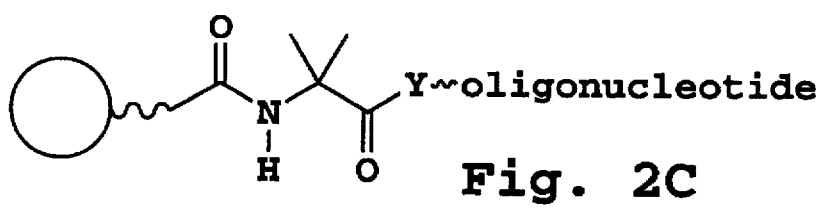
Figure 2D:
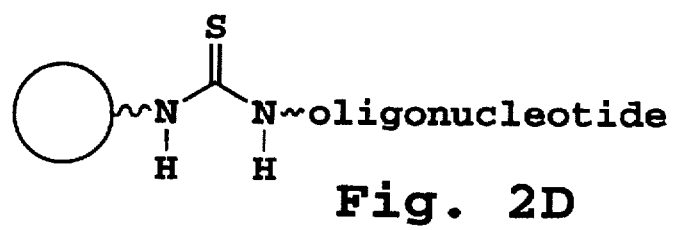
Figure 2E:
Figure 2F:
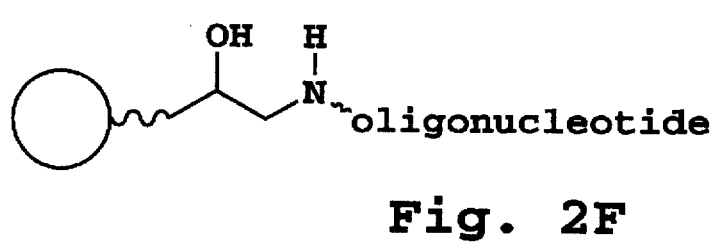
Figure 2G:
Figure 2H:
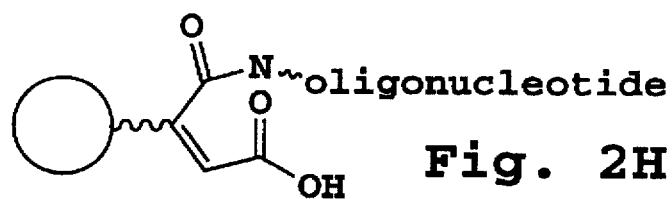
Figure 2I:
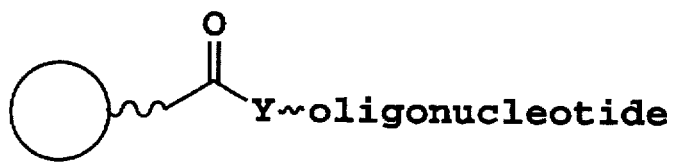
Figure 2J:
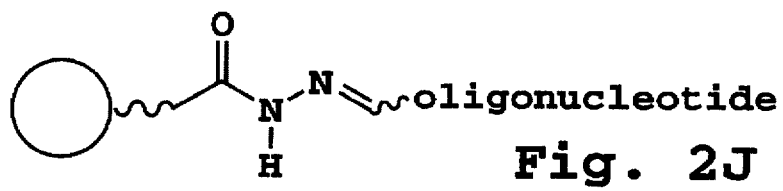
Figure 2K:

Although any suitable functional group fulfilling the desired criteria above may be used to attach the oligonucleotide to the support, preferred linkages include disulfide (FIG. 2G), carbamate (FIG. 2B), hydrazone (FIG. 2J), ester (FIGS. 2C, 2I and 2K, where Y equals oxygen), (N)-functionalized thiourea (FIG. 2D), functionalized maleimide (FIG. 2A, where Y equals sulfur, oxygen, or nitrogen), streptavidin or avidin/biotin (FIG. 2L), mercuric-sulfide (FIG. 2E), gold-sulfide (FIG. 2M), amide (FIGS. 2C, 2I and 2K, where Y equals nitrogen), thiolester (FIGS. 2C, 2I and 2K, where Y equals sulfur). Other suitable functionalities for attaching to a solid support material include azo, ether, and amino.

The immobilization attachment site may be located (i) as a substituent along the modified primer backbone (e.g., derivatization occurring at a terminal 5'-hydroxyl position) or (ii) as a substituent on one of the bases or sugars of the modified primer.

Solid support materials for use in coupling to an oligonucleotide include functionalized supports such as the 1,1'-carbonyldiimidazole activated supports available from Pierce (Rockford, Ill.) or functionalized supports such as those commercially available from Chiron Corp. (Emeryville, Calif.). Solid supports for use in the present invention include matrix materials such as 6% cross-linked agarose, Trisacryl GF-2000 (a hydrophilic matrix material) and TSK HW-65F, all activated with 1,1'-carbonyldiimidazole (Pierce). Immobilization is typically carried out by reacting a free amino group of an amino-modified oligonucleotide with the reactive imidazole carbamate of the solid support. Displacement of the imidazole group results in formation of a stable N-alkyl carbamate linkage between the oligonucleotide and the support as shown in FIG. 2B. Coupling is usually carried out at pHs ranging from 9–11 although a pH range from 9.5–10 is preferable. Coupling to pH sensitive materials may be carried out in buffer at pHs around 8.5.

Amino-modified oligonucleotides for use in attaching to a solid support may be synthesized using standard solid phase DNA synthesis methodologies employing, for example, the modified nucleoside phosphoramidite Amino-Modifier-dT (Glen Research, Sterling Va.), which contains a base labile trifluoroacetyl group protecting a primary amine attached to thymine via a 10-atom spacer arm, phosphoramidite 5'-Amino-Modifier C6 (Glen Research, Sterling Va.), which contains a primary amino group protected with an acid labile monomethoxytrityl group, or N-trifluoroacetyl-6-aminohexyl-2-cyanoethyl N',N'-isopropylphosphoramidite (Applied Biosystems, Foster City, Calif.). Although amino-containing oligonucleotides are most commonly prepared using phosphoramidite chemistry, any other method which leads to oligonucleotides containing primary amine groups may also be used.

Amino-modified oligonucleotides are readily transformed to the corresponding thiol or carboxyl-terminated derivatives for use in immobilization or spacer arm attachment reactions requiring 5'-functionalities other than amino. Amino-modified oligonucleotides may be converted to the corresponding carboxyl derivatives by reaction with succinic anhydride (Bischoff, et al., 1987). If desired, the carboxyl-derivatized primer may be coupled to a bifunctional linker such as 1,6-diaminohexane prior to attachment to the solid support by carrying out the coupling reaction in the presence of an activating agent such as a water soluble carbodiimide.

Thiol-modified oligonucleotides may be prepared by treating the deprotected 5'-amino group of a functionalized oligonucleotide with dithiobis(succinimidylpriopionate), followed by sulfhydryl deprotection with dithioerythritol (Bischoff, et al., 1987).

Oligonucleotides containing free amino, thiol, and hydroxyl functions may also be coupled to supports by utilizing epoxide ring-opening reactions (Maskos, et al., 1992). One such exemplary epoxy-activated solid support is available from Pierce (Rockford, Ill.) and contains 1,4-butanediol diglycidyl ether-activated agarose. Coupling reactions are typically carried out at pHs from 7.5–13, depending upon the stability of the molecule to be immobilized. In immobilization reactions carried out with the above Pierce support, the resulting immobilized oligonucleotide is separated from the solid support by a 13-atom hydrophilic spacer arm.

In another immobilization approach, aldehyde groups of a modified oligonucleotide are coupled to hydrazide groups on a solid matrix as shown in FIG. 2J. A primary hydroxyl group on an oligonucleotide is first oxidized to the corresponding aldehyde, typically with a mild oxidant such as sodium periodate. The oligonucleotide is then coupled to a hydrazide-containing matrix such as Pierce's CarboLink™ Hydrazide. The coupling reaction is performed at neutral pH.

Figure 2M:

Alternatively, the immobilization reaction is carried out using a thiol-derivatized oligonucleotide which is coupled to a functionalized matrix such as Pierce's Immobilized p-Chloromercuribenzoate (FIG. 2E). The support is a cross-linked agarose containing an ethylene diamine spacer and coupling takes place via affinity binding between the mercury and sulfur atoms. Similarly, as shown in FIG. 2M, immobilization may be carried out by anchoring a 5'-thiolated primer to a gold surface (Hegner, et al., 1993a). Using this approach, the modified primer is chemisorbed onto a gold surface (e.g., the solid support) via thiolate bonding. The preparation of polycrystalline gold surfaces has been previously described (Hegner, et al., 1993b).

Functionalization may also be carried out using a homo- or hetero- bifunctional cross-linker, such as Pierce's Sulfo-SMCC. Cross-linkers for use in the present invention will typically contain spacer arms between about 3–20 angstroms in length. Cross-linkers for use in coupling an oligonucleotide to a solid support will typically contain functional groups for targeting reactive primary amines, sulfhydryls, carbonyls, and carboxyls. Cross-linking agents for reaction with primary amino groups will typically contain terminal amidoester groups or N-hydroxysuccinimidyl esters. An exemplary linker such as Pierce's Sulfo-SMCC contains a reactive carboxyl group at one end for coupling to amine-derivatized solid supports such as hexylamine-derivatized polystyrene beads. The other end of the linker molecule contains a reactive maleimide molecule which readily reacts with oligonucleotides containing nucleophilic groups such as hydroxy, thio, or amino. Cross-linkers for reaction with sulfhydryl groups typically contain terminal maleimide groups, alkyl or aryl halides, α-haloacyls or pyridyl disulfides. A variety of chemical cross-linking agents are available from Pierce (Rockford, Ill.).

Alternatively, coated plates, such as those available from Pierce, may be used to immobilize the modified oligonucleotide. Examples of plates for use in immobilizing the oligonucleotides of the invention include activated plates such as Pierce's Reacti-Bind™ Maleic Anhydride Activated Polystyrene Plates and Reacti-Bind™ Streptavidin Coated Polystyrene Plates. A primary amino-containing oligonucleotide is immobilized on the former plate surface by covalent attachment through a stable amide bond formed by reaction between the free amino group of the oligonucleotide and the reactive anhydride (FIG. 2H). The latter plates are effective for affinity binding of biotinylated oligonucleotides. Gold-coated plates may also be utilized for binding to thiol-derivatized primers.

Biotinylated oligonucleotides for use in immobilization to streptavidin or avidin-coated solid supports are prepared as described in Example 2A and shown in FIG. 2L. A variety of biotinylation reagents are commercially available (e.g., Pierce) which are functionalized to react with molecules such as modified oligonucleotides containing primary amino, sulfhydryl, or carbohydrate groups.

Returning to Example 2A, an amino-modified primer is treated with biotin or with a modified form of biotin containing an intervening spacer arm, such as NHS-SS-Biotin (Pierce), or NHS-LC-Biotin (Pierce), a biotin derivative containing an eleven carbon spacer arm between biotin and a terminal N-hydroxylsuccinimide activated carboxyl group. The biotinylated primer is then immobilized by attachment to a streptavidin-coated support. Due to the strong non-covalent biotin/streptavidine interaction, the immobilized primer is considered to be essentially irreversibly bound to the solid support. This is one preferred immobilization attachment for use in the present invention, as the resulting immobilized complex is unaffected by most extremes of pH, organic solvents, and other denaturing agents (Green, 1975). An alternative to avidin(streptavidin)-biotin immobilization is incorporation of a digoxigenin molecule (Sigma, St. Louis, Mo.) in the modified primer with subsequent capture using anti-digoxigenin antibodies.

Enzymatic methods may also be utilized for coupling an oligonucleotide to a solid support (Goldkorn, et al., 1986). In one exemplary embodiment, a poly(dA) tail is added to the 3' ends of a double stranded DNA using 3'terminal transferase. The (dA)-tailed DNA is then hybridized to oligo(dT)-cellulose. To covalently link the DNA to the solid support, the hybridized sample is first reacted with a Klenow fragment of DNA polymerase I, followed by treatment with T4 DNA ligase. The unligated strand of DNA is separated from the immobilized strand by heating followed by extensive washing. The method results in ssDNA covalently linked by its 5' end to a solid support.

The modified primers of the present invention may also be affixed onto a gold surface. In utilizing this immobilization approach, oligonucleotides modified at the 5'-end with a linker arm terminating in a thiol group are chemisorbed with high affinity onto gold surfaces (Hegner, et al., 1993a). Thiolated primers, available through post solid-phase synthesis modification using commercially available reagents (Pierce, Rockford Ill.), are immobilized on a thin layer of gold either prior to or following enzymatic extension. The gold layer is deposited onto the sample stage for direct analysis by mass spectrometry following internal cleavage and evaporation. Alternatively, the resulting extension segments may be transferred onto an alternate surface prior to analysis.

III. REACTIONS EMPLOYING THE IMMOBILIZED CLEAVABLE OLIGONUCLEOTIDE COMPOSITION

A. HYBRIDIZATION AND EXTENSION

The method employed for determining the sequence of a target oligonucleotide strand will often involve Sanger-type sequencing using the modified cleavable primers of the present invention. Immobilization of the modified primer on the solid support may take place either before or after the enzymatic extension reactions.

Utilizing the Sanger DNA sequencing procedure, dideoxynucleotides of each of the four bases are obtained for inclusion into the reaction mixture. The dideoxy nucleotides are incorporated into DNA by, for example, E. coli DNA polymerase since they have a normal 5' triphosphate group. Once incorporated into the growing DNA strand, the dideoxynucleotide triphosphate (ddNTP) cannot form a phosphodiester bond with the next incoming dNTP and growth of the DNA chain is terminated.

A typical DNA sequencing reaction using the Sanger method proceeds as follows. The reaction consists of a target DNA strand to be sequenced, a modified primer containing a cleavable site in accordance with the invention, and that is complementary to the end of the target strand, a carefully controlled ratio of one particular dideoxynucleotide with its normal deoxynucleotide counterpart, and the three other deoxynucleotide triphosphates. The modified primer may or may not be immobilized to the solid support at this point. (Immobilization may occur either before of after the enzymatic extension reactions, depending on a number of experimental factors).

DNA polymerase is added and normal polymerization begins from the primer. Upon incorporation of a ddNTP, the growth of the chain is stopped. A series of different strands results, the lengths of which are dependent on the location of a particular base relative to the end of the DNA. The target strand is usually distributed into four DNA polymerase reactions, each containing one of the four ddNTPs and a modified primer of the present invention. The extension reaction is then carried out as described above.

Sanger-type DNA sequencing is generally carried out using a DNA sequencing kit such as "SEQUENASE" Version 1.0 or Version 2.0 T7 DNA Polymerase (United States Biochemical, Cleveland OH). The "SEQUENASE" Version 1.0 kit uses a chemically-modified DNA polymerase derived from bacteriophage T7 DNA polymerase in which the high 3'-5' exonuclease activity of the native T7 DNA polymerase is inactivated.

In using the USB "SEQUENASE" kit, double stranded templates are first denatured (if one is using double stranded template), and the primer is then hybridized or annealed to the target by heating for 2 min at 65° C., followed by slow cooling to less than 35° C. over about 15–30 minutes. Supercoiled plasmid DNAs are denatured by treatment with sodium hydroxide, neutralized, and ethanol-precipitated in order to anneal the primer for sequencing.

Termination mixtures containing the different ddNTPs are prepared for use in the termination reactions. The annealed DNA mixture is optionally labeled, and the labeled reaction mixture is added to each of the four termination tubes. In the present invention, extension reactions are carried out to produce a distribution of products ranging from near zero to several hundreds of base pairs in length. Optionally, a stop solution (containing formamide, EDTA, bromophenol blue, and xylene cyanol FF) is added to stop the reactions prior to analysis of the resultant samples.

For reactions in which the modified primers were not immobilized to a solid support prior to enzymatic extension, immobilization is carried out as described in Section IIB above.

The immobilized extended primers are then washed to remove excess enzymes, ions, salts, and other impurities. In one embodiment, the extended primers are immobilized onto the surface of microtitre wells. Immobilization to the solid support facilitates product purification and subsequent isolation by cleavage of the primer at the cleavage site followed by removal in the supernatant.

Alternately, DNA sequencing may be carried out using deoxynucleoside α-thiotriphosphates, dNTPαSs (available from United States Biochemical, Cleveland Ohio), followed by limited exonuclease-promoted base-specific digestion, such as with Exonuclease III (New England BioLabs, Beverly Mass.) or snake venom phosphodiesterase (Boehringer Mannheim, Mannheim, Germany) (Olsen, D., et al., 1993). Cleavage of DNA fragments specifically at positions of incorporated phosphorothioate groups may also be carried out using chemical reagents such as 2-iodoethanol or 2,3-epoxy-1propanol (Nakamaye, et al., 1988).

Briefly, the sequencing of a target DNA sequence using the modified primers of the present invention via the incorporation of phosphorothioate nucleosides is carried out as follows. A target DNA sequence is hybridized with a modified primer as described above. The primer is then extended enzymatically in the presence of one deoxynucleoside α-thiotriphosphate (dNTPαS) to generate a mixture of primer extension products containing phosphorothioate linkages. The primer extension products are then treated with a reagent that cleaves specifically at the phosphorothioate linkages, such as exonuclease, 2iodoethanol, or 2,3-epoxy-1-propanol, under conditions effective to produce limited cleavage and resulting in the production of a group of primer extension degradation products.

The primer extension degradation products are immobilized at the immobilization attachment sites to produce immobilized primer extension degradation products, each containing a primer and an extension segment. Alternatively, immobilization may be carried out either i) prior to enzymatic extension, ii) after enzymatic extension, or iii) prior to treating the phosphorothioate-containing primer extension products with a phosphorothioate-specific cleaving reagent.

Subsequent to immobilization, the primer extension degradation products are washed to remove non-immobilized species. Cleavage at the cleavable site results in the release of extension segments, which are then sized by mass spectrometry. Using the sequencing method of this aspect of the invention, the read length of any given extension segment is increased relative to the read length of its corresponding primer extension degradation product.

The steps of hybridization, enzymatic extension, treatment with a phosphorothioate-cleaving reagent, immobilization, washing, cleaving, and sizing are then repeated with a second, third, and fourth of the four different dNTPαS analogs to determine the sequence of the target DNA by comparison of the sizes of the extension segments obtained from each of the four extension reactions.

In an alternate embodiment of the invention, target DNA for sequencing is amplified using the polymerase chain reaction or PCR (Mullis, 1987; Mullis, et al., 1987; Kusukawa, et al., 1990; Gyllensten, 1989). Briefly, PCR amplification is typically carried out by thermocycling a cocktail containing the target DNA of interest, a mixture of deoxynucleotide triphosphates (dNTPs), a reaction buffer, each of two primers, and an extension enzyme such as Taq DNA polymerase (United States Biochemical, Cleveland Ohio) (Erlich, 1989; Innis, 1990). A PCR run profile typically consists of a 5-minute denaturation step at 94° C., followed by 30 cycles of 15 seconds at 94° C., 15 seconds at the annealing temperature, and 1 minute at 72° C. Following thermocycling, the samples can be maintained at 4° C. until removal from the thermocycler. Annealing temperatures range from about 55° C. to 65° C., although most target sequences amplify well at 60° C.

Amplification is followed by hybridization with the modified primers of the present invention, enzymatic extension and sequencing of the products as described above.

B. CLEAVAGE

Cleavage of the selectively cleavable site is carried out as described in Section II A and in Examples 1 A–D and Example 3. Returning to this aspect of the invention, internucleoside silyl groups such as trialkylsilyl ether and dialkoxysilane are cleaved by treatment with fluoride ion. Base-cleavable sites for use in the present invention include β-cyano ether, 5'-deoxy-5'-aminocarbamate, 3'-deoxy-3'-aminocarbamate, urea, 2'-cyano-3', 5'-phosphodiester, 2'-amino-3', 5'-phosphodiester, ester and ribose. Thio-containing internucleotide bonds such as 3'-(S)-phosphorothioate and 5'-(S)-phosphorothioate are cleaved by treatment with silver nitrate or mercuric chloride. Acid cleavable sites for use in the present invention include 3'-(N)-phosphoramidate, 5'-(N)-phosphoramidate, dithioacetal, acetal and phosphonic bisamide. An α-aminoamide internucleoside bond is cleavable by treatment with isothiocyanate, and titanium is used to cleave a 2'-amino-3',5'-phosphodiester-O-ortho-benzyl internucleoside bond. Vicinal diol linkages are cleavable by treatment with periodate. Thermally cleavable groups include allylic sulfoxide and cyclohexene while photo-labile linkages include nitrobenzylether and thymidine dimer.

Cleavage conditions are utilized which leave the immobilization attachment site intact, so that a major portion of the primer remains affixed to the solid support. Preferably, cleavage of the cleavable site results in primer extension products containing five or fewer base pairs from the primer sequence. This maximizes the amount of sequence information provided upon subsequent analysis.

C. ANALYSIS

Any of a number of size fractionating devices may be used to determine the sequence of a target oligonucleotide fragment. Size fractionation methods for use in the present invention include gel electrophoresis, such as polyacrylamide or agarose gel electrophoresis, capillary electrophoresis, mass spectrometry, and HPLC.

In methods employing gel electrophoresis sizing and analysis, the DNA fragments are typically labeled with either radioisotopes or with attached fluorophores, and visualized using autoradiography or fluorescence detection, respectively.

The modified primers of the present invention are particularly advantageous when they are used to generate oligonucleotide fragments whose sizes are to be resolved using technologies that currently have difficulty resolving fragments of over about 100 base pairs differing by one nucleotide in length, such as mass spectrometry.

One preferred method for oligonucleotide analysis using the modified oligonucleotide composition of the invention is mass spectrometry, and particularly matrix-assisted laser desorption ionization (MALDI) mass spectrometry, carried out on a time-of-flight (TOF) mass spectrometer (Wu, et al., 1993). MALDI mass spectrometry provides a rapid and efficient method for oligonucleotide sequencing.

MALDI-TOF mass spectrometry may be used to provide unfragmented mass spectra of mixed-base oligonucleotides containing more than 100 base pairs. Moreover, mass spectral resolution of sequences currently to at least about 40 base pairs in length may be attained.

In this method, pulsed ultraviolet laser light is used to desorb an oligonucleotide out of an absorbing solid matrix, which causes creation of free, unfragmented, charged oligomers. Mass analysis is done in a time-of-flight mass spectrometer. Singly charged molecular ions are typically the most abundant species and fragment ions are not clearly observed.

In preparing the sample for analysis, the analyte is mixed into a matrix of molecules which resonantly absorb at the laser wavelength. Solid matrix materials for this use include 3-hydroxypicolinic acid, α-cyano-4-hydroxycinnamic acid (Youngquist, et al., 1994), nicotinic acid (Hillenkamp, 1988), and ice (Nelson, et al., 1989), although a preferred material is 3-hydroxypicolinic acid.

Examples 4 and 5 include detailed descriptions of MALDI-TOF mass spectral analyses of modified oligonucleotide compositions according to the present invention.

As described in Example 3, a synthetic 17-mer DNA probe containing a cleavable ribose in the 7-position was selectively cleaved by ammonium hydroxide treatment. Mass spectra of the intact mixed base primer prior to (FIG. 3A) and after (FIG. 3B) ammonium hydroxide treatment reveal the selective cleavage of the ribose linkage. As shown in FIG. 3A, two sizable peaks were observed for the intact 17-mer corresponding to the di-protonated molecular ion $[M+2H]^{2+}$ and the protonated molecular ion $[M+H]^{+}$. Following ammonium hydroxide treatment, peaks corresponding to the expected cleavage products, the 7-mer, the 10-mer, and intact 17-mer, were readily observable and identifiable, as illustrated in FIG. 3B.

Figure 4:
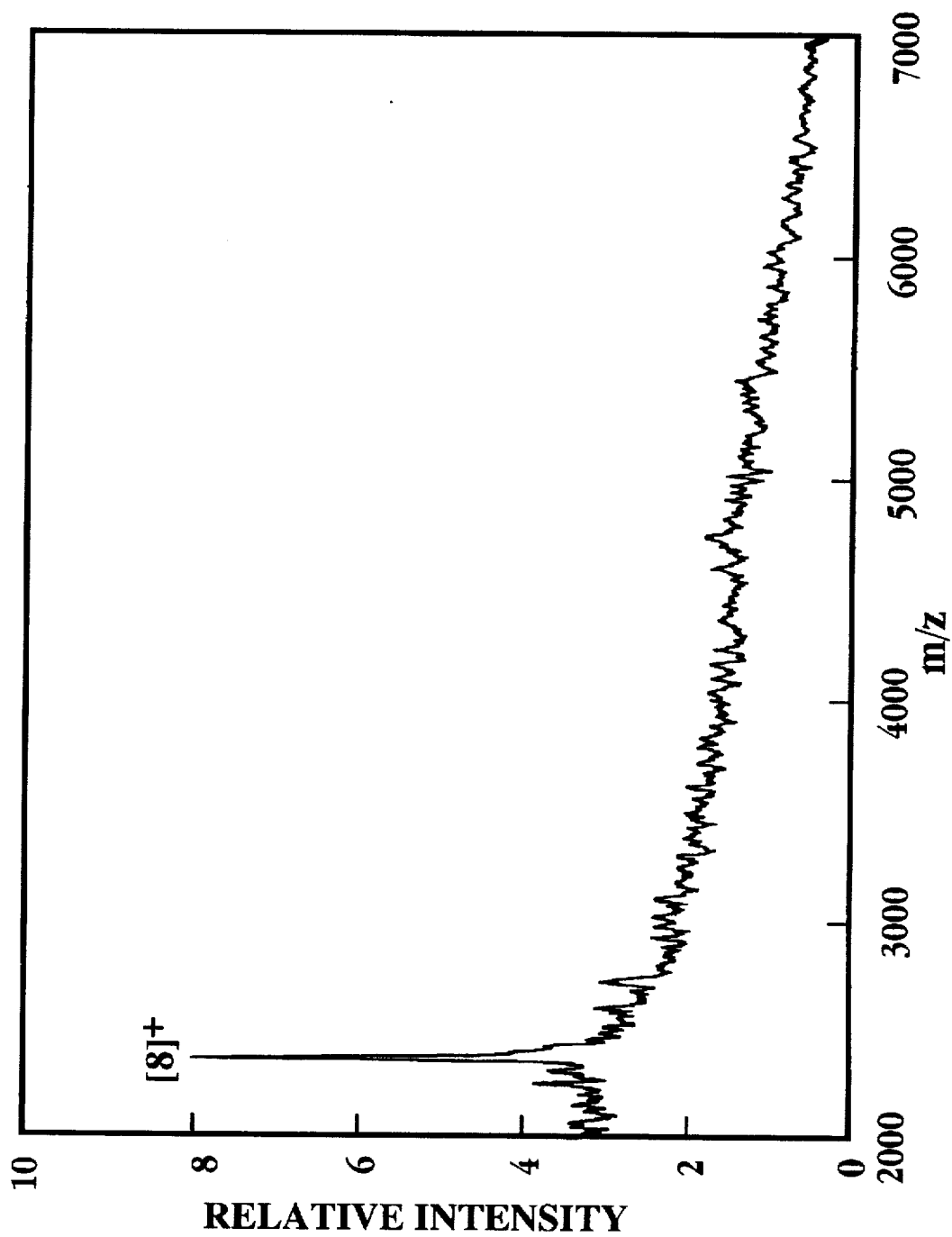
FIG. 4 is a time-of-flight mass spectrum of the cleavage product of an immobilized 18-mer containing a cleavable ribose at the 10-position.

Similarly, mass spectral analysis was carried out on a biotinylated 18-mer containing a ribose in the 10 position and captured on streptavidin-coated beads, as described in Example 5. The immobilized primer was washed after surface binding, followed by treatment with ammonium hydroxide to effect selective cleavage of the immobilized primer at the ribose site. FIG. 4 illustrates the mass spectrum of the 8-mer resulting from selective cleavage of the ribose site within the immobilized primer.

IV. UTILITY

A. GENOMIC SEQUENCING

The method of the present invention may be used for both "shotgun-type" sequence analysis and "directed walk". In the shotgun approach, a random sequence of DNA is selected and used to prime on an unknown target. This approach uses large numbers of primers to increase the possibility of successfully hybridizing with an unknown target sequence. In one embodiment of this approach, a multi-well assay format is used where each well has a different primer and the same substrate (i.e., the target DNA molecule) is added to each well under hybridization conditions. The primers in the wells are the modified primers of the present invention where immobilization to the well surface is through the primer immobilization site. Primer extension reactions are carried out. Extension products are only formed in wells where complementary sequences exist between the primer and the substrate. Each well is examined for the presence of extension products. Extension products are then sequenced and sequences assembled for any given target DNA molecule based on the known sequences of the primers that yielded extension products and base sequence overlap from the extension product sequences (i.e., alignment of the extension product sequences). In using the modified primers of the present invention, the amount of sequence information for the extension segments is maximized over that obtained with similar techniques employing conventional primers, due to cleavage and removal of a large portion of the primer prior to fragment analysis (e.g., increased read lengths). Further, the method, when coupled with analysis by mass spectrometry, is fast and can provide large amounts of data in a relatively short period of time.

In a related approach, the present method may be used to sequence short reads of cDNA inserts for purposes of gene mapping and identification. These short reads of sequence identify each insert uniquely and are called Expressed Sequence Tags or ESTs. In preparing a cDNA library, cDNA copies of mRNAs are first inserted into a standard cloning vector such as pBlueScript. A modified primer according to the present invention is designed to hybridize to the pBlueScript vector sequence with its 3' end immediately adjacent to the cDNA insert. Primer extension and sequencing reactions are then carried out which read into the insert and identify its sequence. In order to identify a unique length of sequence, a minimum read length for the extension segment is typically 20 bases, although a preferred read length is at least about 40 bases.

In an alternative embodiment, an array of the immobilized, cleavable primers can be formulated (Fodor, et al., 1991; Southern, et al., 1992). In this aspect of the invention, the array consists of the modified primers of the present invention where the cleavable linkage is, for example, a photocleavable linkage (e.g., thymine-thymine dimer) and the primer is attached to the support matrix through the immobilization site of the modified primer. In this embodiment, the target DNA molecule is hybridized to the primers, primer extension reactions carried out and the different sequence primers are sequentially cleaved and the presence or absence of an extension product is determined. When extension products are detected their sequences can be determined as described above.

In the directed walk approach, a known DNA sequence is used as the primer sequence, thus providing an initiation point for sequencing in both directions away from the known region. Each newly identified sequence is then used to direct the synthesis of new primers to enable progression of the sequence walk.

B. DIAGNOSTICS

A number of synthetic oligonucleotides are available or may be readily synthesized which are complementary to target nucleic acid sequences (e.g., RNA or DNA) and may be used as probes to detect the presence of certain bacteria, viruses, fungi, parasites and the like.

The oligonucleotide composition of the present invention may be used, for example, to detect the presence of specific DNA or RNA sequences corresponding to the following targets (i) herpes viruses such as cytomegalovirus (CMT), Epstein Bart, and Simplex Herpesvirus; (ii) hepatitis viruses such as hepatitus A, B, G, and D; (iii) papillomaviruses such as human papilloma virus 6, 11, 16, 18, and 33; (iv) retroviruses such as human immunodeficiency virus 1 (HIV I), HIV II, human T-cell lymphoblastic virus I (HTLV I), HTLV II; (v) animal viruses such as pig parvovirus and pig mycoplasma hypneumoniae, parvoviruses such as parvovirus B 19; (vi) picornaviruses such as rhinovirus (enterovirus) and rhinovirus HRV 2-14; (vii) bacteria such as mycobacterium avium, mycobacterium tuberculosis, chlamydia trachomatis, *escherichia coli*, streptococci and staphylococci; and (viii) parasites such as trypanosoma, toxoplasma, and plasmodia.

Modified primers of the present invention having the primer sequence, sequences specifically hybridizable to nucleic acids from the microorganism of interest, are hybridized to nucleic acids in a sample. Primer extension reactions and isolation of extension products is carried out as described above. Presence of the extension product indicates the presence of nucleic acid from the microorganism in the sample. The modified primers and sizing method of the present invention provide a method for rapid, high throughput screening for the presence of specific, target sequences using mass spectrometry.

In a related embodiment, the modified primers of the invention can be used to identify pathogens by direct sequencing. In one such approach, a particular region of genomic DNA is identified which has segments that are common among a large population of pathogens (e.g., conserved regions) located next to regions that contain unique sequences for each pathogen (e.g., variable regions). One such exemplary sequence is from DNA that is transcribed into bacterial 16 S ribosomal RNA, or 16 S rRNA (Olsen, G. J., et al., 1992). All 16 S-like rRNAs contain the same core structure. Nucleotides which are conserved in 90% of the available bacterial 16 S rRNA sequences have been identified (Schmidt, et al., 1994).

Pathogen identification using rRNAs as described above is carried out as follows. In accordance with the present invention, a primer is constructed to hybridize to a select region of the 16 S rRNA consensus sequence, for example, sequence 1047–1065 in 16 S rRNA, where i) the primer has the sequence SEQ. ID NO:9, and ii) reads into the hypervariable region, e.g., sequence 995–1046. Upon analysis of the primer extension segments by mass spectrometry, a single pathogen, if present, can be uniquely identified by determining the sequence along the hypervariable region, with a desirable read length of at least 20 bases, and preferably, at least 40.

Alternatively, instead of selecting a conserved region adjacent a hypervariable region, a series of unique primers can be created that will hybridize to a hypervariable or unique region of a selected pathogen. Enzymatic extension of these primers provides sequence information about an adjacent segment of the hypervariable region. This methodology enables specific identification of each pathogen sequence present in a mixed population. Utilizing this approach, one may target different hypervariable regions for each target pathogen. This approach may be preferred for identifying viruses for which there is often very little conservation among other viruses or bacteria.

In addition to determining the presence of a nucleic acid in a sample from such microorganisms, the present invention facilitates the determination of the specific sequences present in a sample. For example, specific variants of HIV or trypanosomes can be identified as well as the presence or absence of genes responsible for antibiotic resistance.

The modified primers can likewise be used in diagnostic methods where mutant sequences are distinguished from wild-type sequences by sequence variations, such as, deletions, insertions, point mutations. Numerous potential target sites can be evaluated by this method including target sites selected from DNA sequences that vary in length (e.g., BCR/ABL) as well as those that vary in sequence (e.g., sickle cell anemia). The sizing methodology of the present invention is particularly suited for the former application (e.g., target sites of varying length). Hybridizations of the modified primers to target nucleic acids are carried out according to standard procedures, with suitable adjustment of the hybridization conditions to allow modified primer hybridization to the target region.

Use of the modified primers of the present invention for detection of genetic disorders has been described above using the examples of sickle cell anemia and $\alpha$1-antitrypsin deficiency (Watson, et al., 1992). Modified primers used for detecting such disorders typically contain a cleavable site located near the end of the primer, where the end of the primer is upstream from the known mutation site (e.g., within about 20 base pairs from a mutation site detected in a 40-mer).

Another diagnostic example is the detection of BCR-ABL transcripts, which are found in the majority of chronic myelogenous leukemia (CML) patients and in $Ph^+$acute lymphocytic leukemia patients, and are believed to be necessary for the maintenance of leukemic phenotype (Szczylik, et al., 1991; Gale, et al.; Collins, et al., 1984; Daley, et al.). The BCR-ABL transcripts are the result of a translocation of the proto-oncogene ABL (chromosome 9) to the breakpoint cluster region (BCR) (chromosome 22), resulting in the formation of BCR-ABL hybrid genes. In this embodiment, the modified primers of the present invention would have their 3' end before the breakpoint region. Primer extension reactions would then proceed across the breakpoint region if present, or continue through the normal transcript region if no breakpoint was present. The sequence of such primer extension products are diagnostic of whether a breakpoint fusion exists in any given sample of nucleic acids.

The modified primers can also be employed in DNA amplification reactions (e.g., Mullis; Mullis, et al.) for detecting the presence of specific sequences in samples by sizing or sequencing or for preparing quantities of DNA for sequencing reactions. In this embodiment of the invention, modified primers containing immobilization sites that can be attached to the solid support following amplification are particularly useful (e.g., biotin and digoxigenin). Amplified products can be captured, the modified primers cleaved, and the resulting amplification products isolated.

In particular, the present method may be utilized to identify pathogens by the sizing of PCR products. Briefly, primers are first selected to hybridize with a sequence unique to the target pathogen(s) of interest. The primers are chosen for use in a multiplex situation (e.g., one in which several different pathogens may be present) to produce PCR products of varying sizes, with each size correlating to a unique PCR product for a specific pathogen.

Such an experiment for determining the presence of three different pathogens (e.g., *Pseudomonas aeruginosa*, *Escherichia coli*, and *Staphylococcus aureus*) is carried out by adding to a sample containing, in addition to a DNA analyte, modified primers for each of the above pathogens designed to produce PCR amplification products having sizes of, for example, 65, 70, and 75 base pairs, respectively.

The PCR products are reduced in size by as many as 20–25 nucleotides by cleavage at the cleavable site (in the modified primer). This results in shifting the corresponding peaks into a more readily resolvable range of the mass spectrometer and permits multiplexing of greater numbers of PCR products.

The cleaved-amplification products are detected and sized using mass spectrometry, according to the method of the present invention.

The following examples illustrate, but in no way are intended to limit the scope of the present invention.

Materials and Methods

Protected nucleotide H-phosphonates such as Bz-DMT-deoxyadenosine H-phosphonate, iBu-DMT-deoxyguanosine H-phosphonate, fully protected deoxynucleoside phosphoramidites, protected deoxynucleotide diesters and triesters, nucleotide dimers, and solid phase supports may be purchased from Sigma Chemical Co. (St. Louis, Mo.). Bis(trifluoromethanesulfonyl)diisopropylsilane may be purchased from Petrarch Systems Inc. (Bertram, Pa.). Phosphoramidites may be purchased from Applied Biosystems (Foster City, Calif.). Standard chemical reagents and solvents may be purchased from Aldrich Chemical Company (St. Louis, Mo.).

EXAMPLE 1

Preparation of a Modified Oligonucleotide Containing a 3'-5'-Cleavable Linkage

Nucleoside dimers containing the following 3'-5'-internucleoside cleavable linkages are prepared as follows.
A. 3', 5'-Dialkoxysilane Internucleoside Linkage The 3'-O-functionalized nucleoside intermediate, 3'-O-(diisopropylsilyl)-2'-deoxynucleoside triflate (1) is prepared by first adding bis(trifluoromethanesulfonyl)diisopropylsilane (1 mmol) to an equimolar amount of the sterically hindered base, 2,6-di-tert-butyl-4-methylpyridine, dissolved in dry acetonitrile, under an inert atmosphere. The resulting solution is cooled to –40° C. in a cooling bath, to which is added a solution of a 5'-O-protected nucleoside, 5'-(dimethoxytrityl)-2'-deoxynucleoside (0.9 mmol) and 2,6-di-tert-butyl-4-methylpyridine (0.25 mmol) in dimethylformamide over a 10 minute period. The resulting reaction mixture is stirred at –40° C. for 1 hour and then allowed to warm to room temperature. The 3'-O-diisopropylsilyl triflate product is isolated by precipitation from water, with yields typically ranging from 90–100%. Isolation is not required, and preferably, the reactive intermediate is coupled directly with unprotected nucleoside to form the desired dimer.

The above procedure is used to form the 3'-silyl derivatives of the protected nucleosides (dimethoxytrityl) thymidine, N6-benzoyl-2'-deoxy-5'-O-(DMT)adenosine, N4-benzoyl-2'-deoxy-5'-O-(DMT)cytidine, and N2-isobutyrl-2'-deoxy-5'-O-(dimethoxytrityl)guanosine with minimal formation of the undesired 3',3' symmetrical dimers.

Intermediate (1) is reacted with nucleoside, such as thymidine, by stirring a mixture of (1) and nucleoside for approximately 1 hour at room temperature. The coupled dimer is isolated by adding the reaction mixture dropwise to a vigorously-stirred ice/water mixture. The mixture is filtered to give a white solid, which is then dried and purified by column chromatography on silica gel (eluent: ethyl acetate/hexane gradient). The protected dimer, 5'-O-(DMT)-3'-O-(5'-O-nucleosidyldiisopropylsilyl)thymidine (2), is typically isolated in yields ranging from 50–75%.

The prepared dimers are then functionalized for use in automated solid phase synthesis to form primers containing a dialkoxysilane cleavable site.

The dimer, such as (2) above, is converted to the corresponding 3'-(2-cyanoethyl-N,N-diisopropylphosphoramidite) by dissolving the 5'-DMT dimer in tetrahydrofuran and adding the resulting solution dropwise to a stirred solution containing 4-DMAP (4-dimethylaminopyridine), diisopropylethylamine and 2-cyanoethyl-N,N-diisopropylphosphoramidochloridite in THF under nitrogen and maintained at room temperature. The reaction mixture is stirred for 2 h, added to ethyl acetate, washed with brine, and dried over magnesium sulfate. The crude product is then purified by column chromatography on silica using 1:1 ethyl acetate/hexane as the eluent.

The phosphoramidite-functionalized dimer is then employed for use in automated solid phase synthesis using a programmable DNA synthesizer to form an oligonucleotide primer containing a 3'-5'-diisopropylsilyl ether cleavable site.

Cleavage: After carrying out the desired hybridization and extension reactions with an immobilized primer containing a dialkoxysilane internucleotide linkage as described above, the silyl-ether (Si—O) linkage is selectively cleaved by treatment with fluoride ion (Green, 1975) to release the extension product, typically containing no more than about five nucleotides derived from the modified primer molecule.
B. 3'(S)-Phosphorothioate Internucleoside Linkage The functionalized nucleoside, 5'-O-monomethoxytrityl-3'-S-thiophosphoramidate, is prepared as follows. The 3'-S-functionalized starting material, 5'-O-monomethyoxytrityl-3'-S-benzoyl-3'thymidine (3), is prepared according to the method of Cosstick, et al. (Cosstick, et al., 1988). Debenzoylation is carried out by treating a solution of 5'-0-monomethoxytrityl3'-S-benzoyl-3'-thymidine dissolved in argon-saturated ethanol and maintained at 5° C. with 10N sodium hydroxide. The resulting solution is stirred for approximately 1 h. The product, 5'-O-MMT-3'-thiothymidine (4), is purified by column chromatography on silica gel. The 5'-O-MMT-3'-thiothymidine (4) is then converted to the corresponding thiophosphoramidite by reaction with 2-cyanoethyl-N,N-diisopropylaminophosphomonochloridite under standard conditions (McBride, et al., 1983). The 3'-S-thiophosphoramidite (5) is suitable for coupling to a second nucleoside to form a dimer containing a cleavable phosphorothioate site or for use in automated solid phase synthesis to prepare an oligonucleotide containing a phosphorothioate internucleoside linkage.

Chemical synthesis of the phosphorothioate dimer is carried out as follows. A solution of 3'-O-acetylthymidine in acetonitrile is added dropwise over a 20 minute period to a stirred solution of the 3'-S-thiophosphoramidite (5) in acetonitrile saturated with 5-(4-nitrophenyl)tetrazole. Use of the tetrazole activating agent reduces the probability of the self-condensation reaction occurring between two thiophosphoramidite molecules. The resulting thiophosphite dimer (6) is oxidized in situ by quenching the reaction mixture with 2,6-lutidine, followed by addition of an oxidant such as TBA periodate in dichloromethane. The fully protected phosphorothioate dimer (7) is deprotected by treatment with t-butylamine, 80% aqueous acetic acid, followed by concentrated aqueous ammonia to yield the 3'(S)-phosphorothioate-linked thymidine dimer (8).

Formation of an oligonucleotide probe containing a 3'-(S)phosphorothioate cleavable linkage is performed by solid phase synthesis on controlled pore glass using a DNA synthesizer. The protocol and reaction conditions for conducting the solid phase reaction cycle are adjusted according to the primer products desired using standard solid phase phosphoramidite procedures. The functionalized 3'-S-thiophosphoramidite nucleoside (5), prepared as described above, is utilized to introduce the 3'(S)-phosphorothioate moiety into the oligonucleotide primer in the presence of the functionalized tetrazole reagent, 5-(para-nitrophenyl) tetrazole.

Cleavage: After carrying out hybridization, extension, and washing of an immobilized modified primer containing a 3'(S)-phosphorothioate internucleotide bond, selective cleavage of the phosphorus-sulfur bond is carried out by treatment with aqueous silver nitrate.

C. 5'(S)-Phosphorothioate Internucleoside Linkage

Synthesis of an oligonucleotide containing a 5'-phosphorothioate internucleoside linkage is carried out by first synthesizing a derivatized phosphoramidite, 5'-(S-trityl)-mercapto-5'-deoxythymidine-3'-O-(2-cyanoethyl-N,N-diisopropylamino)phosphite as described below.

5'-O-p-toluenesulfonyl thymidine (9) is prepared by reacting thymidine with one equivalent of p-toluenesulfonyl chloride in pyridine. The reaction mixture is stirred for 3 h at room temperature, cooled in ice and quenched by addition of water. Following dissolution in ethyl acetate, and sequential washing with sodium bicarbonate and brine, the solution is dried over sodium sulfate and the solvent is removed in vacuo. The desired 5'-tosylate product (9) is readily recrystallized from ethyl acetate/methanol, thus avoiding the need for a protecting group at the 3'-OH position.

The 5'-tosylate is then converted to the corresponding 5'-(S-trityl)-mercapto-5'-deoxythymidine (10). A solution of the 5'-O-tosylthymidine (9) in ethanol is added to a reaction flask containing a five-fold molar excess of 7.0M sodium hydroxide and triphenylmethyl mercaptan in ethanol (which generates the corresponding reactive thiolate in situ). The reaction mixture is refluxed for 8 hours under an inert atmosphere, filtered to remove residual solids, dissolved in ethyl acetate, and the solution is washed, dried, and evaporated in vacuo. The crude product is purified by chromatography on silica gel using a methanol/methylene chloride gradient.

The desired reactive nucleoside phosphoramidite, 5,-(S-trityl)-mercapto-5'-deoxythymidine-3'-O-(2-cyanoethyl-N,N-diisopropylamino)phosphite (11), is prepared by treating a solution of the protected nucleoside, 5,-(S-trityl)-mercapto-5'-deoxythymidine (10), in dry 1:1 acetonitrile/methylene chloride with an equimolar amount of tetrazole, followed by addition of a 1.5 molar excess of 2-cyanoethyoxy-bis-(N,N-diisopropylamino)phosphine. The reaction mixture is stirred for about 1 hour at room temperature and subsequently quenched by addition of butanol. The solution is diluted with ethyl acetate, washed, dried over anhydrous sodium sulfate, filtered, and evaporated to dryness. The crude product is purified by flash chromatography.

Incorporation of the desired 5'(S)-phosphorothioate cleavable site into an oligonucleotide probe is carried out by utilizing standard solid phase phosphoramidite chemistry.

D. 5'(N)-Phosphoramidate Internucleoside Linkage

Oligonucleotide fragments containing a 5'-N phosphoramidate internucleotide bond are prepared as follows.

Thymidine is transformed to the corresponding 5'-azide derivative (12) by treatment with sodium azide and triphenylphosphine in carbon tetrabromide according to the procedure of Hasa, et al. (Hasa, et al., 1976). Reduction of 5'-azido-5'-deoxythymidine (12) is then carried out by hydrogenation over Pd/C catalyst to form the corresponding 5'-amino derivative (13).

Formation of the corresponding 5'-N-protected nucleoside is carried out by dissolving (3) (25 mmol) in anhydrous pyridine (150 ml), to which is added 4-DMAP (17 mmol), triethylamine (17 mmol), and 4-methoxytrityl chloride (60 mmol), and the resulting reaction mixture is stirred for 2 h at room temperature. Methanol is added to the reaction flask and the resulting mixture is added to a solution of saturated sodium bicarbonate, extracted with chloroform, and the organic extracts dried over anhydrous sodium sulfate. The organic layer is evaporated to dryness and the resulting crude residue is purified by column chromatography over silica gel to yield 5'-amino-5'-deoxy-5'-N-(4-methoxytrityl) thymidine (13). (Cleavage of the N-MeOTr protecting group is carried out by treatment with 3% dichloroacetic acid in 1,2-dichloroethane).

The desired functionalized nucleoside, 5'-amino5'-deoxy-5'-N(4-methoxytrityl)thymidine-3'-(2-cyanoethyl)-N,N-diisopropylphosphoramidite) (14), containing a reactive phosphoramidite moiety suitable for incorporation into an oligonucleotide fragment is synthesized as follows.

The 5'-amino-protected thymidine (13) (4 mmol) is dissolved in anhydrous methylene chloride (60 ml), to which is added dry bis(diisopropylammonium)tetrazolide (3 mmol) and (2-cyanoethoxy)bis(diisopropylamino)phosphine (8 mmol). The mixture is stirred for 1 hour at room temperature, poured into a saturated sodium bicarbonate solution, and extracted several times with chloroform. The combined organic extracts are rinsed with brine, dried, and evaporated to dryness. The crude residue is dissolved in a minimal amount of methylene chloride and precipitated by addition of pentane to yield a mixture of the diastereomeric product, 14.

The functionalized nucleoside 14 is then selectively introduced into an oligonucleotide fragment to form an oligonucleotide containing a 5'-N-phosphoramidate cleavable site. The 5'-amino nitrogen of thymidine derivative 14 is the reactive center at which phosphoramidate bond formation takes place. The modified nucleoside 14 is introduced in the course of a standard cycle into a growing DNA fragment synthesized on a solid support as follows. Insertion of the phosphoramidate group is performed at a specific site to form the desired nucleotide fragment containing a selectively cleavable site.

Formation of the following modified exemplary sequence: d(T-T-C-A-T-G-C-A-A-(phosphoramidate)-T-C-C-G-A-T-G) (SEQ ID NO:1) is performed as follows. The DNA fragment is synthesized in a stepwise fashion beginning from the hexamer sequence d(C-C-G-A-T-G) (Gromova, 1987). The hexamer is synthesized on controlled pore glass as solid support using standard procedures (Bannwarth, et al., 1986; Bannwarth, 1987). The introduction of key intermediate 14 is performed during a standard cycle utilizing slightly longer times for the coupling of 14 and for deblocking of the 4-methoxytrityl protecting group. Following cleavage of the 5'-MeOTr group of 14, the synthesis is continued using standard phosphoramidites as the building units to form the desired 16-mer sequence.

The support material is treated with concentrated ammonia at 56° C. overnight to cleave the 16-mer product from the solid support. Following removal of the support material, the ammonia is removed by vacuum evaporation, and the remaining residue is dissolved in water/dioxane and subsequently precipitated by addition of THF. The resulting 16-mer is then purified by either gel electrophoresis or HPLC.

Selective chemical cleavage of the phosphoramidate internucleotide bond is carried out under mild acidic conditions to form the corresponding phosphate and amino-functionalized fragments. Treatment with 80% acetic acid at room temperature for between 2-6 hours results in selective cleavage of the internucleotide phosphoramidate bond while leaving the unmodified portion of the DNA fragment intact.

EXAMPLE 2

Attachment to the Solid support

A. Streptavidin Affinity Immobilization

A modified primer from Example 1 above containing a cleavable site is immobilized by attachment to a functionalized solid support material. In some cases the cleavable site-containing primer is modified as described below.

For attaching an oligonucleotide primer to a streptavidin-coated support a biotinylated primer is typically used. Biotinylation is carried out as follows.

A primer containing a cleavable site is prepared as in Example 1, with a minor modification: the primer is synthesized to contain a reactive amino site for biotinylation. An amino group is introduced during solid phase synthesis using a standard DNA synthesizer, such as Applied Biosystems 393 DNA/RNA Synthesizer.

To selectively introduce the internal amino function, the modified nucleoside phosphoramidite Amino-Modifier dT, containing a base labile trifluoroacetyl group protecting a primary amine attached to thymine with a 10 atom spacer arm, is added at an appropriate phase of the DNA synthesis cycle. Upon completion of the oligonucleotide synthesis, the primer is cleaved from the support by standard methods. The remaining base-protecting groups as well as the trifluoroacetyl amino protecting group are removed by treatment with fresh, concentrated ammonium hydroxide at 40° for 15-17h. The solution is dried by rotary evaporation, and the residue is redissolved in 200 µl of water.

The amino-modified primer (approximately 0.25 µmol) is reacted with NHS-LC-Biotin (Pierce, Rockford Ill.) which has an 11 carbon spacer between the biotin group and the N-hydroxylsuccinimide activated carboxyl group. Aliquots of a 50mM NHS-LC-biotin solution in DMF are added to the primer solution containing 0.1M sodium bicarbonate/sodium carbonate buffer at pH 9 over a 1.5 h period. The solution is maintained at room temperature overnight and the biotinylated primer is then purified by reverse phase HPLC.

The biotinylated primer is then immobilized by attachment to streptavidin-coupled magnetic beads (Dynabeads M-280, Dynal, Inc., Great Neck, N.Y.) as described in Dynabeads M-280 Technical Handbook: Magnetic DNA Technology 6, Dynal Inc. A neodymium-iron-boron magnet is used to immobilize the beads during supernatant removal and washing steps.

B. Immobilization via a Thiourea Linkage

5'-Amino-modified oligonucleotide primers containing a cleavable linkage are prepared as described in Examples 1 and 2A above.

Glass slides are activated in a two-stage process for coupling to amino-functionalized oligonucleotides. The glass surface is first functionalized by reaction with aminopropyltrimethoxysilane to form an amino-derivatized surface. To carry out the amino-functionalization, clean microscope slides are immersed for 2 minutes in a 1% solution of 3-aminopropyltrimethoxysilane solution in 95% acetone/water. The slides are then washed several times with acetone (5 minutes per wash), and dried for 45 minutes at 110° C.

Following amino-derivatization, the glass slides are treated with excess p-phenylenediisothiocyanate to convert the amino groups to amino-reactive phenylisothiocyanate groups suitable for coupling to amino-functionalized oligonucleotides. The amino-derivatized glass plates are treated for 2 hours with a solution of 0.2% 1,4-phenylene diisothiocyanate solution in 10% pyridine/DMF, followed by washing with methanol and acetone.

A 2 mM solution of the amino-modified primer in sodium carbonate/bicarbonate buffer (2 µL) is applied directly to the activated glass plate surface and the resulting slides are then incubated at 37° C. in a covered Petri dish containing a minimal amount of water for about 2 h. The plates containing thiourea-linked primer are then washed sequentially with 1% ammonium hydroxide, and water, followed by air drying at room temperature.

C. Immobilization via Hg-S Affinity Binding

An amino-modified oligonucleotide primer is prepared as described above. Conversion of the 5'-amino group to a thiol is carried out by reacting 5.0 $A_{260}$ units of the amine-containing primer dissolved in 1.0 ml of 0.2 molar 4-(2-hydroxyethyl)-1-piperazineethanesulfonic acid (pH 7.7) with 1.6 ml of 10 mM dithiobis(succinimidylpropionate) in dry acetonitrile for 1 hour at 20° C. An additional 1.0 ml of 10 mM dithiobis(succinimidylpriopionate) in acetonitrile is then added to the reaction vessel and the resulting mixture is stirred for an additional hour. Addition of dithioerythritol (3.5 ml of a 20 mM solution in 0.2M Tris buffer) is followed by stirring for 1 hour at 37° C. The thiol-derivatized primer solution is concentrated under vacuum to form a concentrate which is further purified using reverse phase HPLC followed by lyophilization.

In an alternate approach for synthesizing thiol-modified oligonucleotide primers, the 5'-phosphate of an oligonucleotide primer is esterified with 6-mercapto-hexanol using a β-cyanoethyl-phosphoramidite C6-Thiol-Modifier (Clontech Laboratories, Inc., Palo Alto, Calif.).

The thiol-derivatized primer is then immobilized on p-chloromercuribenzoate derivatized agarose by mixing a solution of the thiol-derivatized primer (0.25 $A_{260}$ units) dissolved in 140 µl of 1.0 M sodium chloride, 1.0 mM ethylenediaminetetraacetic acid disodium salt (EDTA), and 50 mM Tris HCl (pH 8) with 50 µl of p-chloromercuribenzoate derivatized agarose for 3 minutes at 20° C.

EXAMPLE 3

Selective Cleavage of a Synthetic DNA Probe Containing a Cleavable Ribose

A synthetic DNA probe containing a cleavable ribose site was selectively cleaved by ammonium hydroxide treatment.

The 17-mer, having the sequence: 5'-AAA TAC ATC riboGCT TGA AC-3' was prepared to contain a cleavable ribose in the 7-position. The modified probe was treated with aqueous 3% ammonium hydroxide for 15 minutes at room temperature (pH 10) to effect selective cleavage of the ribose moiety.

EXAMPLE 4

Mass Spectral Analysis of the Selective Cleavage Products of a Ribose-Containing DNA Probe The cleavage products from Example 3 were analyzed using matrix assisted laser desorption with concomitant ionization (MALDI) in conjunction with time-of-flight (TOF) mass spectrometry.

The experimental apparatus used for analyzing the sample fragments was composed of an excitation source, a sample manipulator and a TOF mass spectrometer. The excitation sources used for desorption were a Nd:YAG laser (model DCR-1, Spectra-Physics, Mountain View, Calif.) with spatially filtered 5 ns pulses frequently tripled to 355 nm or quadrupled to 266 nm and a 35-ps pulse Nd:YAG laser (model PY610C-10, Continuum, Santa Clara, Calif.) operating at 355 nm. Both of the lasers were operated at a 10 Hz repetition rate, with a 5 nm pulse width. The desorption laser beam maintained at an incident angle of 45° was focused onto the sample with a 250 mm focal length quartz lens to an elliptical spot size of approximately 100 by 150 µm. A Glan-laser polarizer (Newport Corporation, Fountain Valley, Calif.) was placed in a rotation stage in the beam path for continuously variable attenuation, allowing adjustment of the polarized Nd:YAG laser energy density from below 1 mJ/cm$^2$ to 100 mJ/cm$^2$. The optimum energy density for desporption was found to be in the range of 2 to 20 mJ/cm$^2$.

Sample preparation was carried out as follows. The oligonucleotide fragments were dissolved in deionized water at room temperature to concentrations of about 50 µmol/liter. A separate saturated solution of 3-hydroxypicolinic acid (3-HPA) in 50% water/acetonitrile was freshly prepared, and the two solutions were mixed to provide a sample solution containing 3HPA and analyte in a molar ratio of about 10,000:1. A 2 µL aliquot of the sample solution was pipetted onto the sample stage and spread to an area of 2 mm diameter. The sample was dried under a gentle flow of nitrogen prior to insertion into the vacuum system.

The sample stage, consisting of either a smooth silver foil or a polished silicon wafer, was mounted on a manipulator which allows three translational and one rotational degrees of freedom. The experiments were carried out at room temperature. The sample region was evacuated by a 300 liter per second turbomolecular pump. The drift and detection regions were evacuated using a cryopump with nominal 1500 liter per second pumping speed. The base pressure of the chamber was $3 \times 10^{-9}$ Torr, and the normal working pressure, within about five minutes of sample introduction, was $5-10^{-8}$ Torr.

The ions produced during desorption were extracted perpendicular to the sample surface into the time-of-flight mass spectrometer by biasing the sample with a voltage of 28 kV, with the drift and extraction potentials at ground. The sample-extractor distance was 5 mm, and an einzel lens about 5 cm from the sample was used to focus the ions. Both linear and reflecting TOF mass spectrometric geometries were examined. For reflecting TOF-MS, a two stage electrostatic reflector was used and the effective drift path was 2.0 m. A dualmicrochannel plate detector was used. The detector was placed beside the electrostatic deflector due to space constraints of the vacuum chamber. Deflecting voltage was applied to horizontal deflecting plates and the beam path was bent by 4° in order to direct the ions to the detector for the linear geometry. The total flight distance was 1 m for the linear geometry. The four degree bend was sufficient to block the line-of-sight between the ion creation region and the detector to prevent any energetic neutral flux created in the ionization region from reaching the detector. For reflecting TOF measurements, the beam path was bent by 4° in the opposite direction. To avoid detector saturation caused by the high abundance of ionized matrix molecules in experiments performed at higher laser powers, the low mass matrix ions were deflected away from the detector by a pulsed electric field of 200 V/cm.

The signal output of the microchannel plates was amplified and then digitized with a time resolution of 10 to 50 ns/channel and typically summed over 100 laser pulses. Mass calibration was performed by analyzing a variety of known masses, such as alkalis at low mass, isotopically resolved fullerenes, mixtures of gramicidin S, bovine insulin, horse heart cytochrome C, and horse heart myoglobin.

The resulting time-of-flight mass spectra are illustrated in FIGS. 3A and 3B. FIG. 3A is a mass spectrum of the 17-mer synthetic mixed base primer containing a cleavable ribose linkage prior to ammonium hydroxide treatment. Two sizable peaks were observed for the intact 17-mer corresponding to the di-protonated molecular ion [M+H]$^+$ and the protonated molecular ion, [M+H]$^+$.

The resulting oligomer fragments obtained following ammonium hydroxide treatment were then analyzed, as shown in FIG. 3B. As indicated in the mass spectrum, peaks corresponding to the expected cleavage products, the 7-mer, the 10-mer, and intact 17-mer, were readily observable (and identifiable).

EXAMPLE 5

Capture and Selective Cleavage of a Biotinylated Primer Having a Cleavable Ribose in the 10 Position A biotinylated 18-met containing a ribose in the 10 position, 5'-biotin AT CTT CCT GriboGC AAA CTC A-3' (Keystone Laboratories, Inc., Menlo Park, Calif.), was captured on streptavidin-coated beads (DynaBeads M-280, Dynal, Inc., Great Neck, N.Y.). The immobilized primer was then washed after surface binding, followed by treatment with ammonium hydroxide as described in Example 3 above to effect selective cleavage of the immobilized primer at the ribose site.

The modified primer, containing the biotin immobilization attachment site and the cleavable ribose site, was analyzed both prior to capture and subsequent to selective cleavage. The samples were analyzed using MALDI in conjunction with TOF mass spectrometry, as described in Example 4 above. FIG. 4 illustrates the mass spectrum of the 8-mer resulting from selective cleavage of the ribose site within the immobilized primer.

While the invention has been described with reference to specific methods and embodiments, it will be appreciated that various modifications and changes may be made without departing from the invention.

It is claimed:

1. A method for determining the size of a primer extension product, comprising
    (a) hybridizing a primer with a target nucleic acid, where said primer (i) is complementary to said target nucleic acid; (ii) has a first region containing the 5' end of the primer and an immobilization attachment site, and (iii) has a second region containing the 3' end of the primer, where the 3' end is capable of serving as a priming site for enzymatic extension and where said second region contains a selected cleavable site,
    (b) extending the primer enzymatically to generate a polynucleotide mixture containing an extension product composed of the primer and an extension segment;
    (c) cleaving said extension product at the cleavable site to release said extension segment, where prior to said cleaving the primer is immobilized at said immobilization attachment site; and (d) sizing the extension segment by mass spectrometry, whereby said cleaving is effective to increase the read length of the extension segment relative to the read length of the product of (b).

2. The method of claim 1, where the cleavable site is located at or within about five nucleotides from the 3' end of said primer.

3. The method of claim 2, where the second region of said primer is a single nucleotide that also contains the cleavable site.

4. The method of claim 3, where said second region is a ribonucleotide.

5. The method of claim 1, where the cleavable site is selected from the group consisting of dialkoxysilane, 3'-(S)-phosphorothioate, 5'-(S)phosphorothioate, 3'-(N)-phosphoramidate, 5'-(N)phosphoramidate, and ribose.

6. The method of claim 1, where the enzyme for extending the primer in step (b) is a DNA polymerase.

7. The method of claim 1, which further comprises washing the immobilized product prior to said cleaving step.

8. The method of claim 1, where said sizing is by time-of-flight mass spectrometry.

9. The method of claim 8, wherein said sizing is accomplished by matrix-assisted laser desorption ionization mass spectrometry.

10. The method of claim 9, wherein said extension segment is embedded in a chemical matrix prior to said sizing.

11. The method of claim 1, where said primer is immobilized on a solid support by attachment at the immobilization attachment site to an intervening spacer arm bound to the solid support.

12. The method of claim 11, wherein said intervening spacer arm is six or more atoms in length.

13. The method of claim 1, wherein the immobilization attachment site occurs as a substituent on one of the bases or sugars of the DNA primer.

14. The method of claim 1, where said immobilization attachment site is biotin or digoxigenin.

15. The method of claim 1, where said primer is immobilized on a solid support selected from the group consisting of glass, silicon, polystyrene, aluminum, steel, iron, copper, nickel and gold.

16. A method for determining the size of a primer extension product, comprising (a) combining first and second primers with a target nucleic acid under conditions that promote the hybridization of the primers to the nucleic acid, thus generating primer/nucleic acid complexes, where said first primer (i) is complementary to said target nucleic acid; (ii) has a first region containing the 5' end of the primer and an immobilization attachment site, and (iii) has a second region containing the 3' end of the primer, where the 3' end is capable of serving as a priming site for enzymatic extension and where said second region contains a cleavable site, and where said second primer is homologous to said target nucleic acid, (b) converting the primer/nucleic acid complexes to double-stranded fragments in the presence of a suitable polymerase and all four dNTPs, (c) amplifying the primer-containing fragments by successively repeating the steps of (i) denaturing the double-stranded fragments to produce single-strand fragments, (ii) hybridizing the single strands with the primers to form strand/primer complexes, (iii) generating double-stranded fragments from the strand/primer complexes in the presence of DNA polymerase and all four dNTPs, and (iv) repeating steps (i) to (iii) until a desired degree of amplification has been achieved, (d) denaturing the amplified fragments to generate a mixture including a product composed of the first primer and an extension segment;

(e) immobilizing amplified fragments containing the first primer, utilizing said immobilization attachment site, and removing non-immobilized amplified fragments, (f) cleaving said immobilized fragments at the cleavable site to release the extension segment; and (g) sizing the extension segment by mass spectrometry, whereby said cleaving is effective to increase the read length of the extension segment relative to the read length of the product of (d).

17. A method for determining the DNA sequence of a target DNA sequence, comprising (a) hybridizing a primer with a target DNA, where said primer (i) is complementary to said target DNA; (ii) has a first region containing the 5' end of the primer and an immobilization attachment site, and (iii) has a second region containing the 3' end of the primer, where the 3' end is capable of serving as a priming site for enzymatic extension and where said second region contains a cleavable site, (b) extending the primer with an enzyme in the presence of a first of four different dideoxy nucleotides to generate a mixture of primer extension products each product containing a primer and an extension segment;

(c) cleaving at the cleavable site to release the extension segments, where prior to said cleaving the primers are immobilized at said immobilization attachment sites;

(d) sizing the extension segments by mass spectrometry, whereby said cleaving is effective to increase the read length of the extension segment relative to the read length of the product of (b), (e) repeating steps (a) through (d) with a second, third, and fourth of the four different dideoxy nucleotides, and (f) determining the DNA sequence of said target DNA by comparison of the sizes of the extension segments obtained from each of the four extension reactions.

18. A method for determining the DNA sequence of a target DNA sequence, comprising (a) hybridizing a primer with a target DNA, where said primer (i) is complementary to said target DNA; (ii) has a first region containing the 5' end of the primer and an immobilization attachment site, and (iii) has a second region containing the 3' end of the primer, where the 3' end is capable of serving as a priming site for enzymatic extension and where said second region contains a cleavable site, (b) extending the primer with an enzyme in the presence of a first of four different deoxynucleoside α-thiotriphosphate analogs (dNTPαS) to generate a mixture of primer extension products containing phosphorothioate linkages, (c) treating the primer extension products with a reagent that cleaves specifically at the phosphorothioate linkages, where said treating is carried out under conditions producing limited cleavage, resulting in the production of a group of primer extension degradation products, (d) washing the primer extension degradation products, where prior to said washing, the primer extension degradation products are immobilized at said immobilization attachment sites, each immobilized primer extension degradation product containing a primer and an extension segment, where said washing is effective to remove non-immobilized species, (e) cleaving at the cleavable site to release the extension segments, (f) sizing the extension segments by mass spectrometry, whereby said cleaving is effective to increase the read length of any given extension segment relative to the read length of its corresponding primer extension degradation product, (g) repeating steps (a) through (f) with a second, third, and fourth of the four different dNTPαSs, and (h) determining the DNA sequence of said target DNA by comparison of the sizes of the extension segments obtained from each of the four extension reactions.

19. The method of claim 18, wherein the reagent of step (c) is selected from the group consisting of exonuclease, 2-iodoethanol, and 2,3-epoxy-1-propanol.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( v i ) ORIGINAL SOURCE:
        ( C ) INDIVIDUAL ISOLATE: Exemplary 16- mer containing a
        phosphoramidate linkage ( i x ) FEATURE:
        ( A ) NAME/KEY: misc_feature
        ( B ) LOCATION: 9..10
        ( D ) OTHER INFORMATION: /note="sequence contains
        phosphoramidate bond betweeen nucleotides 9 and
        10"

( x i ) SEQUENCE DESCRIPTION: SEQ ID NO:1:

TTCATGCAAT CCGATG         16

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( v i ) ORIGINAL SOURCE:
        ( C ) INDIVIDUAL ISOLATE: Immobilized cleavable 20-mer primer ( i x ) FEATURE:
        ( A ) NAME/KEY: misc_feature
        ( B ) LOCATION: 16..17
        ( D ) OTHER INFORMATION: /note="primer containing a first
        region with an immobilization attachment site, a
        cleavable site "X"between nucleotides 16 and 17

( x i ) SEQUENCE DESCRIPTION: SEQ ID NO:2:

ACTCCTGTGG AGAACTCTGC         20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( v i ) ORIGINAL SOURCE:
 ( C ) INDIVIDUAL ISOLATE: Exemplary single stranded target,
 complement to seq. id no 2

( x i ) SEQUENCE DESCRIPTION: SEQ ID NO:3:

GCAGAGTTCT CCACAGGAGT  20

( 2 ) INFORMATION FOR SEQ ID NO:4:

( i ) SEQUENCE CHARACTERISTICS:
 ( A ) LENGTH: 16 base pairs
 ( B ) TYPE: nucleic acid
 ( C ) STRANDEDNESS: single
 ( D ) TOPOLOGY: linear ( i i ) MOLECULE TYPE: DNA (genomic)

( i i i ) HYPOTHETICAL: YES ( i v ) ANTI-SENSE: NO ( v i ) ORIGINAL SOURCE:
 ( C ) INDIVIDUAL ISOLATE: Immobilized primer subsequent to
 selective cleavage ( x i ) SEQUENCE DESCRIPTION: SEQ ID NO:4:

ACTCCTGTGG AGAACT  16

( 2 ) INFORMATION FOR SEQ ID NO:5:

( i ) SEQUENCE CHARACTERISTICS:
 ( A ) LENGTH: 19 base pairs
 ( B ) TYPE: nucleic acid
 ( C ) STRANDEDNESS: single
 ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
 ( C ) INDIVIDUAL ISOLATE: portion of alpha1-antitrypsin gene,
 posns 333- 352(wild type)

( x i ) SEQUENCE DESCRIPTION: SEQ ID NO:5:

ACCATCGACG AGAAAGGGA  19

( 2 ) INFORMATION FOR SEQ ID NO:6:

( i ) SEQUENCE CHARACTERISTICS:
 ( A ) LENGTH: 7 amino acids
 ( B ) TYPE: amino acid
 ( C ) STRANDEDNESS: single
 ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
 ( C ) INDIVIDUAL ISOLATE: fragment of protein produced by
 alpha1- antitrypsin gene (wild type)

( x i ) SEQUENCE DESCRIPTION: SEQ ID NO:6:

Thr Ile Asp Glu Lys Gly Thr
1               5

( 2 ) INFORMATION FOR SEQ ID NO:7:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: portion of alpha1-antitrypsin gene
        w/ single point mutation ( x i ) SEQUENCE DESCRIPTION: SEQ ID NO:7:

ACCATCGACA AGAAAGGGA                                              19

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( C ) INDIVIDUAL ISOLATE: portion of protein formed by mutant
        alpha1- antitrypsin gene ( x i ) SEQUENCE DESCRIPTION: SEQ ID NO:8:

Thr Ile Asp Lys Lys Gly Thr
1               5

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: rRNA ( i i i ) HYPOTHETICAL: NO ( i v ) ANTI-SENSE: NO ( v i ) ORIGINAL SOURCE:
        ( C ) INDIVIDUAL ISOLATE: primer for region of 16S rRNA
        consensus sequence, 1047-1065

( x i ) SEQUENCE DESCRIPTION: SEQ ID NO:9:

ACGACANCCA TGCANCACC                                              19